(12) United States Patent
Holmdahl et al.

(10) Patent No.: US 7,361,742 B2
(45) Date of Patent: Apr. 22, 2008

(54) METHODS AND MATERIALS FOR TREATING INFLAMMATORY CONDITIONS

(75) Inventors: Rikard Holmdahl, Lund (SE); Lars T. Hellman, Uppsala (SE)

(73) Assignee: Resistentia Pharmaceuticals AB, Uppsala (SE)

( * ) Notice: Subject to any disclaimer, the term of this patent is extended or adjusted under 35 U.S.C. 154(b) by 571 days.

(21) Appl. No.: 10/724,662

(22) Filed: Dec. 1, 2003

(65) Prior Publication Data

US 2004/0214768 A1    Oct. 28, 2004

Related U.S. Application Data

(60) Provisional application No. 60/430,278, filed on Dec. 2, 2002.

(51) Int. Cl.
 *C07K 19/00* (2006.01)
(52) U.S. Cl. .................. 530/402; 530/403; 530/806
(58) Field of Classification Search .................. None
 See application file for complete search history.

(56) References Cited

U.S. PATENT DOCUMENTS

| | | | |
|---|---|---|---|
| 4,683,195 | A | 7/1987 | Mullis et al. |
| 4,873,191 | A | 10/1989 | Wagner et al. |
| 5,580,859 | A | 12/1996 | Felgner et al. |
| 5,589,466 | A | 12/1996 | Felgner et al. |
| 6,534,058 | B2 | 3/2003 | Fung et al. |
| 7,063,847 | B1 * | 6/2006 | Sanderson et al. ....... 424/184.1 |

FOREIGN PATENT DOCUMENTS

| | | |
|---|---|---|
| EP | 0 300 740 | 1/1989 |
| WO | WO 96/39503 | 12/1996 |
| WO | WO 01/15731 | 3/2001 |
| WO | WO 03/015819 | 2/2003 |

OTHER PUBLICATIONS

Stafslien, DK et al. J. Bacteriol. [2000] 182(11):3254-3258.*
Oshima, M et al. Immunol. Lett. [1998] 60:7-12.*
Na, B-K et al. Clin Diag Lab. Immunol. [1999] 6(3):429-433.*
GenBank Accession No. M57729.
Andersson et al., "Collagen-induced arthritis (CIA) is an experimental model for autoimmune arthritis which is induced in rodents by immunization with type II collagen (CII)," *Immunogenetics*, 1992, 35:71-72.
Carney and Hugli, "Site-specific mutations in the N-terminal region of human C5a that affect interactions of C5a with the neutrophil C5a receptor," *Protein Science*, 1993, 2:1391-1399.
Gossler et al., "Transgenesis by means of blastocyst-derived embryonic stem cell lines," *Proc. Natl. Acad. Sci. USA*, 1986, 83:9065-9069.
Hennecke et al., "A detailed analysis of the C5a anaphylatoxin effector domain: selection of C5a phage libraries on differentiated U937 cells," *Eur. J. Biochem.*, 1998, 252:36-44.
Kola et al., "Analysis of the C5a anaphylatoxin core domain using a C5a phage library selected on differentiated U937 cells," *Molecular Immunology*, 1999, 36:145-152.
Lo, "Transformation by Iontophoretic Microinjection of DNA: Multiple Integrations Without Tandem Insertions," *Molecular and Cellular Biology*, 1983, 3:1803-1814.
Mizuno et al., "Comparison of the suppressive effects of soluble CR1 and C5a receptor antagonist in acute arthritis induced in rats by blocking of CD59," *Clin. Exp. Immunol.*, 2000, 119:368-375.
Mulligan et al., "Requirement and Role of C5a in Acute Lung Inflammatory Injury in Rats," *J. Clin. Invest.*, 1996, 98:503-512.
Pellas et al., "Novel C5a Receptor Antagonists Regulate Neutrophil Functions In Vitro and In Vivo," *J. Immunol.*, 1998, 160:5616-5621.
Sambrook et al., *Molecular Cloning*, 1989, 2nd edition, Cold Spring Harbor Laboratory, Plainview, NY, Sections 7.39-7.52.
Schnieke et al., "Human Factor IX Transgenic Sheep Produced by Transfer of Nuclei from Transfected Fetal Fibroblasts," *Science*, 1987, 278:2130-2133.
Siciliano et al., "Two-site binding of C5a by its receptor: An alternative binding paradigm for G protein-coupled receptors," *Proc. Natl. Acad. Sci. USA*, 1994, 91:1214-1218.
Svensson et al., "IL-4-deficient mice develop less acute but more chronic relapsing collagen-induced arthritis," *Eur. J. Immunol.*, 2002, 32:2944-2953.
Thompson et al., :"Germ Line Transmission and Expression of a Corrected HPRT Gene Produced by Gene Targeting in Embryonic Stem Cells," *Cell*, 1989, 56:313-321.
Toth et al., "The pharmacophore of the human C5a anaphylatoxin," *Protein Science*, 1994, 3:1159-1168.
Van der Putten et al., "Efficient insertion of genes into mouse germ line via retroviral vectors," *Proc. Natl. Acad. Sci. USA*, 1985, 82:6148-6152.
Wang et al., "A Role for Complement in Antibody-Mediated Inflammation: C5-Deficient DBA/1 Mice Are Resistant to Collagen-Induced Arthritis," *J. Immunol.*, 2000, 164:4340-4347.
Wang et al., "Anti-C5 monoclonal antibody therapy prevents collagen-induced arthritis and ameliorates established disease," *Proc. Natl. Acad. Sci. USA*, 1995, 92:8955-8959.
Wilken et al., "Specific detection by flow cytometry of histidine-tagged ligands bound to their receptors using a tag-specific monoclonal antibody," *J. Immunol. Meth.*, 1999, 226:139-145.
Zhang et al., "Solution structure of a unique C5a semi-synthetic antagonist: Implications in receptor binding," *Protein Science*, 1997, 6:65-72.
Zhang et al., "Structural Definition of the C5a C Terminus by Two-Dimensional Nuclear Magnetic Resonance Spectroscopy," *PROTEINS: Structure, Function, and Genetics*, 1997, 28:261-267.

* cited by examiner

*Primary Examiner*—Christina Chan
*Assistant Examiner*—F. Pierre VannderVegt
(74) *Attorney, Agent, or Firm*—Fish & Richardson P.C.

(57) ABSTRACT

The invention provides methods and materials for treating inflammatory conditions. Specifically, the invention provides polypeptides, isolated nucleic acids, host cells, and methods that can be used to induce an antibody response in a mammal against an antigen such as C5 or C5a. For example, the methods and materials described herein can be used to reduce the effects of C5a within a mammal by reducing the amount of total and receptor bound C5a in the mammal.

5 Claims, 13 Drawing Sheets

Figure 1

```
gccgctaccagccatgggtctttggggaatactttgtcttttaattttcctggacaaaacttggggaca
ggaacaaacctacgtcatttcagcacccaaaatcctccgggtcggctcgtctgaaaatgtggtaattca
agtccatggctacactgaagcatttgatgcaactctttctctaaaaagctatcctgacaaaaaagtcac
cttctcttcaggctatgttaatttgtccccggaaaacaaattccaaaacgcggcactgttgacactaca
gcccaatcaagttcctagagaagaaagcccagtctctcacgtgtatctggaagttgtgtcaaaacactt
ttcaaaatcaaagaaataccaattacctataacaatggaattctcttcatccatacagacaaacctgt
ttacacgccggaccagtcagtaaagatcagagtctattctctgggtgacgacttgaagccagccaaacg
ggagactgtcttaactttcatagaccccgaaggatcagaagttgacattgtagaagaaatgattacac
cggaattatctcttttcctgacttcaagattccatctaatcccaagtatggtgtttggacaattaaagc
taactataagaaggattttacaacaactggaactgcatactttgaattaaagaatatgtcttgccacg
attctctgtttcaatagaactagaaagaaccttcattggctataaaaactttaagaactttgaaatcac
tgtgaaagcaagatattttataataaagtggtacctgatgctgaagtgtatgccttttttggattgag
agaggacataaaagatgaggagaagcagatgatgcacaaagccacacaagccgcaaagttggttgacgg
agttgctcagatctcttttgattctgaaacagcagttaaagagctgtcctacaacagtctagaagactt
aaacaacaagtacctttatattgcagtaacagtcacagaatcttcaggtggatttttcagaagaggcaga
aatccctggagtcaaatatgtcctctctccctacacactgaatttggtcgctactcctcttttcgtgaa
gcccgggattccattttccatcaaggcacaggttaaagattcactcgagcaggcggtaggagggggtccc
agtaactctgatggcacaaacagtcgatgtgaatcaagagacatctgacttggaaacaaagaggagcat
cactcatgacactgatggagtagctgtgtttgtgctgaacctcccatcaaatgtgacggtgctaaagtt
tgagatcagaactgatgacccagaacttcccgaagaaaatcaagccagcaaagagtacgaagcagttgc
gtactcgtctctcagccaaagttacatttacatcgcttggactgaaaactacaagcccatgcttgtggg
agaatacctgaatattatggttaccccaagagcccatatatcgacaaaataactcactataattactt
gattttatccaaaggcaaaattgtacagtacggcacaagagagaaacttttctcctcaacttatcaaaa
tataaatattccagtgacacagaacatggttccttcagcacgactcctggtctattacatagtcacagg
ggagcaaacagcagaattagtggctgacgcagtctggataaatattgaggagaagtgtggcaaccagct
ccaggtccatctgtctccagatgaatatgtgtattctccaggccaaactgtgtcccttgacatggtgac
tgaagcagactcatgggtagcactatcagcagtggacagagctgtgtataaagtccagggaaacgccaa
aagggccatgcaaagagtcttcaagctttggatgaaaagagtgacctgggctgtggggcaggtggtgg
ccatgacaatgcagatgtattccatctagctgggctcaccttcctcaccaacgcaaacgcagatgactc
ccattatcgtgatgactcttgtaaagaaattctcaggtcaaagagaaacctgcatctcctaaggcagaa
aatagaagaacaagctgctaagtacaaacatagtgtgccaaagaaatgctgctatgacggagcccgagt
gaacttctacgaaacctgtgaggagcgagtggcccgggttaccataggccctctctgcatcagggcctt
caacgagtgctgtactattgcgaacaagatccgaaaagaaagcccccataaacctgtccaactgggaag
gatccacattaagaccctgttaccagtgatgaaggcagatatccgaagctactttccagagagctggct
atgggaaattcatcgcgttcccaaaagaaaacagctgcaggtcacgctgcctgactcactaacgacttg
ggaaattcaaggcattggcatttcagacaatggtatatgtgttgctgatacactcaaggcaaaggtgtt
caaagaagtcttcctggagatgaacataccatattctgttgtgcgaggagaacagatccaattgaaagg
aactgtttacaactatatgacctcagggacaaagttctgtgttaaatgtctgctgtggaggggatctg
cacttcaggaagctcagctgctagccttcacacctccaggccctccagatgtgtgttccagaggataga
gggctcgtccagtcacttggtgaccttcaccctgcttcctctggaaattggccttcactccataaactt
ctcactagagacctcatttgggaaagacatcttagtaaagacattacgggtagtgccagaaggagtcaa
gagggaaagctatgccggcgtgattctggaccctaagggaattcgtggtattgttaacagacgaaagga
attcccatacaggatcccattagatttggtccccaagaccaaagttgaaaggattttgagtgtcaaagg
actgcttgtaggggagttcttgtccacggttctgagtaaggaaggcatcaacatcctaacccacctccc
caagggcagtgcagaggcagagctcatgagcatagctccggtgttctatgttttccactacctggaagc
aggaaaccattggaatattttctatcctgatacactgagtaaaagacagagcctggagaaaaaaataaa
acaagggggtggtgagcgtcatgtcctacagaaacgctgactattcctacagcatgtggaaggggcgag
cgctagtacctggctgacagcttttgctctgagagtgcttggacaggtggccaagtatgtaaaacagga
```

Figure 1

```
tgaaaactcaatttgtaactctttgctatggctggttgagaagtgtcagctggaaaacggctctttcaa
ggaaaattcccaatatctaccaataaaattacagggtactttgcctgctgaagcccaagagaaaacttt
gtatcttacagccttttctgtgattggaattagaaaggcagttgacatatgccccaccatgaaaatcca
cacagcgctagataaagccgactccttcctgcttgaaaacaccctgccatccaagagcaccttcacact
ggccattgtagcctatgctctttccctaggagacagaacccacccgaggtttcgtctaattgtgtcggc
cctgaggaaggaagctttttgttaaaggtgatccgcccatttaccgttactggagagatacccctcaaacg
tccagacagctctgtgcccagcagcggcacagcaggtatggttgaaaccacagcctatgctttgctcgc
cagcctgaaactgaaggatatgaattacgccaacccatcatcaagtggctatctgaagagcagaggta
tggaggcggcttttattccacccaggatacgattaatgccatcgagggcctgacagaatattcactcct
gttaaaacaaattcatttggatatggacatcaatgtcgcctacaaacacgaaggtgacttccacaagta
taaggtgacagagaagcatttcctggggaggccagtggaggtatctctcaatgatgaccttgttgtcag
cacaggctacagcagtggcttggccacagtatatgtaaaaactgtggttcacaaaattagtgtctctga
ggaattttgcagcttttacttgaaaattgatacccaagatattgaagcatccagccacttcaggctcag
tgactctggattcaagcgcataatagcatgtgccagctacaagcccagcaaggaggagtcaacatccgg
gtcctccatgcagtaatggatatatcactgccgactggaatcggagcaaacgaggaagatttacgggc
tcttgtggaaggagtggatcaactactaactgattaccagatcaaagatggccatgtcattctgcaact
gaattcgatcccctccagagatttcctctgtgtccggttccggatatttgaacttttccaagttgggtt
tctgaatcctgctaccttcacggtgtacgagtatcacagaccagataagcagtgcaccatgatttatag
catttctgacaccaggcttcagaaagtctgtgaaggagcagcttgcacatgtgtggaagctgactgtgc
gcaactgcaggcagaagtagacctagccatctctgcagactccagaaaagagaaagcctgtaaaccaga
gactgcatatgcttataaagtcaggatcacatcagccactgaagaaaatgtttttgtcaagtacactgc
gactcttctggtcacttacaaaacaggggaagctgctgatgagaattcggaggtcaccttcattaaaaa
gatgagctgtaccaatgccaacctggtgaaagggaagcagtatttaatcatgggcaaagaggttctgca
gatcaaacacaatttcagtttcaagtatatatacccctctagattcctccacctggattgaatattggcc
cacagacacaacgtgtccatcctgtcaagcatttgtagagaatttgaataactttgctgaagacctctt
tttaaacagctgtgaatgaaaagttctgctgcacgaagattcctcctgcggcgggggattgctcctcc
tctggcttggaaacctagcctagaatcagatacactttctttagagtaaagcacaagctgatgagttac
gactttgtgaaatggatagccttgaggggaggcgaaaacaggtcccccaaggctatcagatgtcagtgc
caatagactgaaacaagtctgtaaagttagcagtcagggtgttggttgggccggaagaagagaccca
ctgaaactgtagccccttatcaaaacatatccttgcttgaaagaaaaataccaaggacagaaaatgcca
taaaatcttgactttgcactc     (SEQ ID NO:1)
```

Figure 2

MetGlyLeuTrpGlyIleLeuCysLeuLeuIlePheLeuAspLysThrTrpGlyGlnGluGlnThrTyr
ValIleSerAlaProLysIleLeuArgValGlySerSerGluAsnValValIleGlnValHisGlyTyr
ThrGluAlaPheAspAlaThrLeuSerLeuLysSerTyrProAspLysLysValThrPheSerSerGly
TyrValAsnLeuSerProGluAsnLysPheGlnAsnAlaAlaLeuLeuThrLeuGlnProAsnGlnVal
ProArgGluGluSerProValSerHisValTyrLeuGluValValSerLysHisPheSerLysSerLys
LysIleProIleThrTyrAsnAsnGlyIleLeuPheIleHisThrAspLysProValTyrThrProAsp
GlnSerValLysIleArgValTyrSerLeuGlyAspAspLeuLysProAlaLysArgGluThrValLeu
ThrPheIleAspProGluGlySerGluValAspIleValGluGluAsnAspTyrThrGlyIleIleSer
PheProAspPheLysIleProSerAsnProLysTyrGlyValTrpThrIleLysAlaAsnTyrLysLys
AspPheThrThrThrGlyThrAlaTyrPheGluIleLysGluTyrValLeuProArgPheSerValSer
IleGluLeuGluArgThrPheIleGlyTyrLysAsnPheLysAsnPheGluIleThrValLysAlaArg
TyrPheTyrAsnLysValValProAspAlaGluValTyrAlaPhePheGlyLeuArgGluAspIleLys
AspGluGluLysGlnMetMetHisLysAlaThrGlnAlaAlaLysLeuValAspGlyValAlaGlnIle
SerPheAspSerGluThrAlaValLysGluLeuSerTyrAsnSerLeuGluAspLeuAsnAsnLysTyr
LeuTyrIleAlaValThrValThrGluSerSerGlyGlyPheSerGluGluAlaGluIleProGlyVal
LysTyrValLeuSerProTyrThrLeuAsnLeuValAlaThrProLeuPheValLysProGlyIlePro
PheSerIleLysAlaGlnValLysAspSerLeuGlnAlaValGlyGlyValProValThrLeuMet
AlaGlnThrValAspValAsnGlnGluThrSerAspLeuGluThrLysArgSerIleThrHisAspThr
AspGlyValAlaValPheValLeuAsnLeuProSerAsnValThrValLeuLysPheGluIleArgThr
AspAspProGluLeuProGluGluAsnGlnAlaSerLysGluTyrGluAlaValAlaTyrSerSerLeu
SerGlnSerTyrIleTyrIleAlaTrpThrGluAsnTyrLysProMetLeuValGlyGluTyrLeuAsn
IleMetValThrProLysSerProTyrIleAspLysIleThrHisTyrAsnTyrLeuIleLeuSerLys
GlyLysIleValGlnTyrGlyThrArgGluLysLeuPheSerSerThrTyrGlnAsnIleAsnIlePro
ValThrGlnAsnMetValProSerAlaArgLeuLeuValTyrTyrIleValThrGlyGluGlnThrAla
GluLeuValAlaAspAlaValTrpIleAsnIleGluGluLysCysGlyAsnGlnLeuGlnValHisLeu
SerProAspGluTyrValTyrSerProGlyGlnThrValSerLeuAspMetValThrGluAlaAspSer
TrpValAlaLeuSerAlaValAspArgAlaValTyrLysValGlnGlyAsnAlaLysArgAlaMetGln
ArgValPheGlnAlaLeuAspGluLysSerAspLeuGlyCysGlyAlaGlyGlyGlyHisAspAsnAla
AspValPheHisLeuAlaGlyLeuThrPheLeuThrAsnAlaAsnAlaAspAspSerHisTyrArgAsp
AspSerCysLysGluIleLeuArgSerLysArgAsnLeuHisLeuLeuArgGlnLysIleGluGluGln
AlaAlaLysTyrLysHisSerValProLysLysCysCysTyrAspGlyAlaArgValAsnPheTyrGlu
ThrCysGluGluArgValAlaArgValThrIleGlyProLeuCysIleArgAlaPheAsnGluCysCys
ThrIleAlaAsnLysIleArgLysGluSerProHisLysProValGlnLeuGlyArgIleHisIleLys
ThrLeuLeuProValMetLysAlaAspIleArgSerTyrPheProGluSerTrpLeuTrpGluIleHis
ArgValProLysArgLysGlnLeuGlnValThrLeuProAspSerLeuThrThrTrpGluIleGlnGly
IleGlyIleSerAspAsnGlyIleCysValAlaAspThrLeuLysAlaLysValPheLysGluValPhe
LeuGluMetAsnIleProTyrSerValValArgGlyGluGlnIleGlnLeuLysGlyThrValTyrAsn
TyrMetThrSerGlyThrLysPheCysValLysMetSerAlaValGluGlyIleCysThrSerGlySer
SerAlaAlaSerLeuHisThrSerArgProSerArgCysValPheGlnArgIleGluGlySerSerSer
HisLeuValThrPheThrLeuLeuProLeuGluIleGlyLeuHisSerIleAsnPheSerLeuGluThr
SerPheGlyLysAspIleLeuValLysThrLeuArgValValProGluGlyValLysArgGluSerTyr
AlaGlyValIleLeuAspProLysGlyIleArgGlyIleValAsnArgArgLysGluPheProTyrArg
IleProLeuAspLeuValProLysThrLysValGluArgIleLeuSerValLysGlyLeuLeuValGly
GluPheLeuSerThrValLeuSerLysGluGlyIleAsnIleLeuThrHisLeuProLysGlySerAla
GluAlaGluLeuMetSerIleAlaProValPheTyrValPheHisTyrLeuGluAlaGlyAsnHisTrp
AsnIlePheTyrProAspThrLeuSerLysArgGlnSerLeuGluLysLysIleLysGlnGlyValVal
SerValMetSerTyrArgAsnAlaAspTyrSerTyrSerMetTrpLysGlyAlaSerAlaSerThrTrp
LeuThrAlaPheAlaLeuArgValLeuGlyGlnValAlaLysTyrValLysGlnAspGluAsnSerIle
CysAsnSerLeuLeuTrpLeuValGluLysCysGlnLeuGluAsnGlySerPheLysGluAsnSerGln

Figure 2

TyrLeuProIleLysLeuGlnGlyThrLeuProAlaGluAlaGlnGluLysThrLeuTyrLeuThrAla
PheSerValIleGlyIleArgLysAlaValAspIleCysProThrMetLysIleHisThrAlaLeuAsp
LysAlaAspSerPheLeuLeuGluAsnThrLeuProSerLysSerThrPheThrLeuAlaIleValAla
TyrAlaLeuSerLeuGlyAspArgThrHisProArgPheArgLeuIleValSerAlaLeuArgLysGlu
AlaPheValLysGlyAspProProIleTyrArgTyrTrpArgAspThrLeuLysArgProAspSerSer
ValProSerSerGlyThrAlaGlyMetValGluThrThrAlaTyrAlaLeuLeuAlaSerLeuLysLeu
LysAspMetAsnTyrAlaAsnProIleIleLysTrpLeuSerGluGluGlnArgTyrGlyGlyGlyPhe
TyrSerThrGlnAspThrIleAsnAlaIleGluGlyLeuThrGluTyrSerLeuLeuLeuLysGlnIle
HisLeuAspMetAspIleAsnValAlaTyrLysHisGluGlyAspPheHisLysTyrLysValThrGlu
LysHisPheLeuGlyArgProValGluValSerLeuAsnAspAspLeuValValSerThrGlyTyrSer
SerGlyLeuAlaThrValTyrValLysThrValValHisLysIleSerValSerGluGluPheCysSer
PheTyrLeuLysIleAspThrGlnAspIleGluAlaSerSerHisPheArgLeuSerAspSerGlyPhe
LysArgIleIleAlaCysAlaSerTyrLysProSerLysGluGluSerThrSerGlySerSerHisAla
ValMetAspIleSerLeuProThrGlyIleGlyAlaAsnGluGluAspLeuArgAlaLeuValGluGly
ValAspGlnLeuLeuThrAspTyrGlnIleLysAspGlyHisValIleLeuGlnLeuAsnSerIlePro
SerArgAspPheLeuCysValArgPheArgIlePheGluLeuPheGlnValGlyPheLeuAsnProAla
ThrPheThrValTyrGluTyrHisArgProAspLysGlnCysThrMetIleTyrSerIleSerAspThr
ArgLeuGlnLysValCysGluGlyAlaAlaCysThrCysValGluAlaAspCysAlaGlnLeuGlnAla
GluValAspLeuAlaIleSerAlaAspSerArgLysGluLysAlaCysLysProGluThrAlaTyrAla
TyrLysValArgIleThrSerAlaThrGluGluAsnValPheValLysTyrThrAlaThrLeuLeuVal
ThrTyrLysThrGlyGluAlaAlaAspGluAsnSerGluValThrPheIleLysLysMetSerCysThr
AsnAlaAsnLeuValLysGlyLysGlnTyrLeuIleMetGlyLysGluValLeuGlnIleLysHisAsn
PheSerPheLysTyrIleTyrProLeuAspSerSerThrTrpIleGluTyrTrpProThrAspThrThr
CysProSerCysGlnAlaPheValGluAsnLeuAsnAsnPheAlaGluAspLeuPheLeuAsnSerCys
Glu (SEQ ID NO:2)

Figure 4 gaattccaccatcaccatcaccatctcgagccgcgggccgatatgaaaatcgaagaaggtaaactggta
atctggattaacggcgataaaggctataacggtctcgctgaagtcggtaagaaattcgagaaagatacc
ggaattaaagtcaccgttgagcatccggataaactggaagagaaattcccacaggttgcggcaactggc
gatggccctgacattatcttctgggcacacgaccgctttggtggctacgctcaatctggcctgttggct
gaaatcaccccggacaaagcgttccaggacaagctgtatccgtttacctgggatgccgtacgttacaac
ggcaagctgattgcttacccgatcgctgttgaagcgttatcgctgatttataacaaagatctgctgccg
aacccgccaaaaacctgggaagagatcccggcgctggataaagaactgaaagcgaaaggtaagagcgcg
ctgatgttcaacctgcaagaaccgtacttcacctggccgctgattgctgctgacgggggttatgcgttc
aagtatgaaaacggcaagtacgacattaaagacgtgggcgtggataacgctggcgcgaaagcgggtctg
accttcctggttgacctgattaaaaacaaacacatgaatgcagacaccgattactccatcgcagaagct
gcctttaataaaggcgaaacagcgatgaccatcaacggcccgtgggcatggtccaacatcgacaccagc
aaagtgaattatggtgtaacggtactgccgaccttcaagggtcaaccatccaaaccgttcgttggcgtg
ctgagcgcaggtattaacgccgccagtccgaacaaagagctggcaaaagagttcctcgaaaactatctg
ctgactgatgaaggtctggaagcggttaataaagacaaaccgctgggtgccgtagcgctgaagtcttac
gaggaagagttggcgaaagatccacgtattgccgccactatggaaaacgcccagaaaggtgaaatcatg
ccgaacatcccgcagatgtccgctttctggtatgccgtgcgtactgcggtgatcaacgccgccagcggt
cgtcagactgtcgatgaagccctgaaagacgcgcagactaattcgagctcgaacaacaacaacaataac
aataacaacaacctcgggatcgagggaaggctgctaaggcagaaaatagaagaacaagctgctaagtac
aaacatagtgtgccaaagaaatgctgctatgacggagcccgagtgaacttctacgaaacctgtgaggag
cgagtggcccgggttaccataggccctctctgcatcagggccttcaacgagtgctgtactattgcgaac
aagatccgaaaagaaagcccccataaacctgtccaactgggaaggtaagtcgag (SEQ ID NO:3)

Figure 5

GluPheHisHisHisHisHisHisLeuGluProArgAlaAspMetLysIleGluGluGlyLysLeuVal
IleTrpIleAsnGlyAspLysGlyTyrAsnGlyLeuAlaGluValGlyLysLysPheGluLysAspThr
GlyIleLysValThrValGluHisProAspLysLeuGluGluLysPheProGlnValAlaAlaThrGly
AspGlyProAspIleIlePheTrpAlaHisAspArgPheGlyGlyTyrAlaGlnSerGlyLeuLeuAla
GluIleThrProAspLysAlaPheGlnAspLysLeuTyrProPheThrTrpAspAlaValArgTyrAsn
GlyLysLeuIleAlaTyrProIleAlaValGluAlaLeuSerLeuIleTyrAsnLysAspLeuLeuPro
AsnProProLysThrTrpGluGluIleProAlaLeuAspLysGluLeuLysAlaLysGlyLysSerAla
LeuMetPheAsnLeuGlnGluProTyrPheThrTrpProLeuIleAlaAlaAspGlyGlyTyrAlaPhe
LysTyrGluAsnGlyLysTyrAspIleLysAspValGlyValAspAsnAlaGlyAlaLysAlaGlyLeu
ThrPheLeuValAspLeuIleLysAsnLysHisMetAsnAlaAspThrAspTyrSerIleAlaGluAla
AlaPheAsnLysGlyGluThrAlaMetThrIleAsnGlyProTrpAlaTrpSerAsnIleAspThrSer
LysValAsnTyrGlyValThrValLeuProThrPheLysGlyGlnProSerLysProPheValGlyVal
LeuSerAlaGlyIleAsnAlaAlaSerProAsnLysGluLeuAlaLysGluPheLeuGluAsnTyrLeu
LeuThrAspGluGlyLeuGluAlaValAsnLysAspLysProLeuGlyAlaValAlaLeuLysSerTyr
GluGluGluLeuAlaLysAspProArgIleAlaAlaThrMetGluAsnAlaGlnLysGlyGluIleMet
ProAsnIleProGlnMetSerAlaPheTrpTyrAlaValArgThrAlaValIleAsnAlaAlaSerGly
ArgGlnThrValAspGluAlaLeuLysAspAlaGlnThrAsnSerSerSerAsnAsnAsnAsnAsnAsn
AsnAsnAsnAsnLeuGlyIleGluGlyArgLeuLeuArgGlnLysIleGluGluGlnAlaAlaLysTyr
LysHisSerValProLysLysCysCysTyrAspGlyAlaArgValAsnPheTyrGluThrCysGluGlu
ArgValAlaArgValThrIleGlyProLeuCysIleArgAlaPheAsnGluCysCysThrIleAlaAsn
LysIleArgLysGluSerProHisLysProValGlnLeuGlyArg (SEQ ID NO:4)

Figure 8

[Plot showing Mean maximum arthritis score: MBP-C5a ~19 (marked **), Control ~38]

METHODS AND MATERIALS FOR TREATING INFLAMMATORY CONDITIONS

CROSS-REFERENCE TO RELATED APPLICATIONS

This application claims priority from U.S. Provisional Application Ser. No. 60/430,278, filed Dec. 2, 2002.

TECHNICAL FIELD

The invention relates to methods and materials involved in treating inflammatory conditions.

BACKGROUND

Rheumatoid arthritis (RA) is an autoimmune, inflammatory condition that affects peripheral joints. Collagen-induced arthritis animal models have helped define genes related to RA conditions. A major histocompatibility complex (MHC) class II gene (Aq in mouse) important for the initiation and maintenance of RA conditions has been identified. This gene functionally corresponds to the HLA-DR gene DR*0401 in humans, suggesting that T cell mediated autoimmune recognition of joint specific antigens is involved in the disease.

Genes in regions outside the MHC also have been found to be important for the initiation and maintenance of RA conditions. One of these gene regions is located on chromosome 2 in mouse and contains a gene coding for the complement factor C5. One of the active components of C5 is C5a, which is released during complement binding to immunocomplexes. The release of C5a triggers several different pathways that lead to rheumatoid inflammation. C5a produced locally in an inflammatory joint can bind to receptors on macrophages and neutrophilic granulocytes, leading to infiltration of inflammatory cells into joints. C5 also plays a central role in complement-mediated processes such as sepsis, myocardial ischemia/reperfusion injury, adult respiratory distress syndrome, nephritis, and graft rejection, as well as complement-mediated inflammatory conditions such as rheumatoid arthritis, asthma, inflammatory bowel disease, multiple sclerosis, arteriosclerosis, and vasculitis.

SUMMARY

The invention relates to methods and materials for treating inflammatory conditions such as sepsis, myocardial ischemia/reperfusion injury, adult respiratory distress syndrome, nephritis, graft rejection, rheumatoid arthritis, asthma, inflammatory bowel disease, multiple sclerosis, arteriosclerosis, and vasculitis in a mammal. Specifically, the invention provides polypeptides, isolated nucleic acids, host cells, and methods for treating inflammatory conditions. Polypeptides of the invention can be immunogenic. In one aspect, the invention provides immunogenic polypeptides that contain both self and non-self amino acid segments. For example, the invention provides a polypeptide that contains a self C5a amino acid segment and one or more non-self T cell epitopes. In another aspect, the invention provides isolated nucleic acids that encode immunogenic polypeptides suitable for treating a mammal with an inflammatory condition. In addition, the invention provides host cells containing isolated nucleic acids encoding polypeptides provided herein. Such host cells can be used to produce large amounts of the encoded polypeptides, for example.

In one aspect, the invention features a composition containing a polypeptide, wherein the polypeptide includes a self C5 amino acid segment and a non-self amino acid segment, and wherein the length of the non-self segment is less than 350 amino acids (e.g., less than 300 amino acids, less than 250 amino acids, or less than 200 amino acids). Administration of the polypeptide to a mammal can induces an anti-C5 response in the mammal, and the genome of the mammal can include a nucleic acid that encodes the self C5 amino acid segment. The non-self amino acid segment can be a bacterial amino acid segment (e.g., an MBP amino acid segment). The non-self amino acid segment can be a C5 amino acid segment. The non-self C5 amino acid segment can be non-naturally occurring. The non-self C5 amino acid segment can contain at least two T cell epitopes. The non-self amino acid segment can be a vertebrate (e.g., mammalian) C5 amino acid segment. The non-self vertebrate C5 amino acid segment can contain at least two T cell epitopes. The non-self amino acid segment can be a viral amino acid segment or a fungal amino acid segment.

The invention also features a method for treating a mammal (e.g., a human) having an inflammatory condition. The method can include administering a polypeptide to the mammal such that the polypeptide induces an anti-C5 response in the mammal, the polypeptide containing a self C5 amino acid segment and a non-self amino acid segment, where the genome of the mammal contains a nucleic acid that encodes the self C5 amino acid segment. The inflammatory condition can be sepsis, myocardial ischemia/reperfusion injury, adult respiratory distress syndrome, nephritis, graft rejection, rheumatoid arthritis, asthma, inflammatory bowel disease, multiple sclerosis, arteriosclerosis, and/or vasculitis. The polypeptide can be MBP-C5a. The self C5 amino acid segment can contain a portion of a C5a sequence. The non-self amino acid segment can contain a portion of a C5 sequence. The non-self amino acid segment can be viral, bacterial, fungal, mammalian, and/or non-naturally occurring. The non-self amino acid segment can contain at least two T cell epitopes.

In another aspect, the invention features a composition containing a polypeptide having a self C5 amino acid segment and a non-self C5 amino acid segment. Administration of the polypeptide to a mammal can induce an anti-C5 response in the mammal, and the genome of the mammal can contain a nucleic acid that encodes the self C5 amino acid segment. The non-self C5 amino acid segment can be non-naturally occurring. The non-self C5 amino acid segment can contain at least two T cell epitopes.

In another aspect, the invention features a composition containing a polypeptide having a self C5 amino acid segment and a non-self vertebrate amino acid segment. Administration of the polypeptide to a mammal can induce an anti-C5 response in the mammal, and the genome of the mammal can contain a nucleic acid that encodes the self C5 amino acid segment. The non-self vertebrate amino acid segment can be a mammalian amino acid segment. The non-self vertebrate amino acid segment can contain at least two T cell epitopes.

In another aspect, the invention features a composition containing a polypeptide that includes a self C5 amino acid segment and a non-self amino acid segment, wherein the length of the non-self amino acid segment is less than 350 (e.g., less than 300, less than 250, or less than 200) amino acid residues. Administration of the polypeptide to a mammal can induce an anti-C5 response in the mammal, and the genome of the mammal can contain a nucleic acid that encodes the self C5 amino acid segment. The non-self amino acid segment can be viral, bacterial, fungal, mammalian, and/or non-naturally occurring. The non-self mammalian amino acid segment can contain at least two T cell epitopes.

In another aspect, the invention features a composition containing a polypeptide and an adjuvant, wherein the polypeptide contains a self C5 amino acid segment and a bacterial amino acid segment. The bacterial amino acid segment can be MBP.

In another aspect, the invention features a composition containing a polypeptide having a self C5 amino acid segment and a fungal amino acid segment.

In another aspect, the invention features a composition containing a polypeptide having a self C5 amino acid segment and a viral amino acid segment.

In another aspect, the invention features an isolated nucleic acid encoding a polypeptide that contains a self C5 amino acid segment and a non-self C5 amino acid segment.

In another aspect, the invention features an isolated nucleic acid encoding a polypeptide that contains a self C5 amino acid segment and a non-self vertebrate amino acid segment.

In yet another aspect, the invention features an isolated nucleic acid encoding a polypeptide that contains a self C5 amino acid segment and a non-self amino acid segment, the length of the non-self amino acid segment being less than 360 (e.g., less than 300, less than 250, or less than 200) amino acid residues.

In another aspect, the invention features an isolated nucleic acid encoding a polypeptide that contains a self C5 amino acid segment and a bacterial amino acid segment, wherein the polypeptide lacks a factor Xa cleavage site between the C5 amino acid segment and the bacterial amino acid segment. The non-self bacterial amino acid segment can be MBP.

In another aspect, the invention features an isolated nucleic acid encoding a polypeptide that contains a self C5 amino acid segment and a fungal amino acid segment.

In another aspect, the invention features an isolated nucleic acid encoding a polypeptide that contains a self C5 amino acid segment and a viral amino acid segment.

Another aspect of the invention features a host cell containing (1) an isolated nucleic acid, where the isolated nucleic acid encodes a polypeptide having a self C5 amino acid segment and a non-self C5 amino acid segment; (2) an isolated nucleic acid, where the isolated nucleic acid encodes a polypeptide having a self C5 amino acid segment and a non-self vertebrate amino acid segment; (3) an isolated nucleic acid, where the isolated nucleic acid encodes a polypeptide having a self C5 amino acid segment and a non-self amino acid segment, the length of the non-self amino acid segment being less than 350 (e.g., less than 300, less than 250, or less than 200) amino acid residues; (4) an isolated nucleic acid, where the isolated nucleic acid encodes a polypeptide having a self C5 amino acid segment and a non-self bacterial amino acid segment; (5) an isolated nucleic acid, where the isolated nucleic acid encodes a polypeptide having a self C5 amino acid segment and a non-self fungal amino acid segment; and/or (6) an isolated nucleic acid, where the isolated nucleic acid encodes a polypeptide having a self C5 amino acid segment and a non-self viral amino acid segment. The host cell can express the polypeptide.

In another aspect, the invention features a composition for administration to a mammal. The composition can contain a polypeptide, wherein with respect to the mammal the polypeptide contains a self C5 amino acid segment and a non-self C5 amino acid segment. Administration of the polypeptide to a mammal can induce an anti-C5 response in the mammal, wherein the genome of the mammal contains a nucleic acid that encodes the self C5 amino acid segment. The non-self C5 amino acid segment can be non-naturally occurring. The non-self C5 amino acid segment can contain at least two T cell epitopes.

In another aspect, the invention features a composition for administration to a mammal, the composition containing a polypeptide, wherein with respect to the mammal the polypeptide includes a self C5 amino acid segment and a non-self vertebrate amino acid segment. Administration of the polypeptide to a mammal can induce an anti-C5 response in the mammal, wherein the genome of the mammal contains a nucleic acid that encodes the self C5 amino acid segment. The non-self vertebrate amino acid segment can be a mammalian amino acid segment. The non-self vertebrate amino acid segment can include at least two T cell epitopes.

In yet another aspect, the invention features a composition for administration to a mammal. The composition can contain a polypeptide, wherein with respect to the mammal the polypeptide includes a self C5 amino acid segment and a non-self amino acid segment, wherein the length of the non-self amino acid segment is less than 350 (e.g., less than 300, less than 250, or less than 200) amino acid residues. Administration of the polypeptide to a mammal can induce an anti-C5 response in the mammal, wherein the genome of the mammal contains a nucleic acid that encodes the self C5 amino acid segment. The non-self amino acid segment can be viral, bacterial, fungal, or mammalian. The non-self amino acid segment can be non-naturally occurring. The non-self mammalian amino acid segment can include at least two T cell epitopes.

In another aspect, the invention features a composition for administration to a mammal, the composition containing a polypeptide and an adjuvant, wherein with respect to the mammal the polypeptide includes a self C5 amino acid segment and a bacterial amino acid segment (e.g., MBP).

In another aspect, the invention features a composition for administration to a mammal, the composition containing a polypeptide, wherein with respect to the mammal the polypeptide includes a self C5 amino acid segment and a fungal amino acid segment.

The invention also features a composition for administration to a mammal, the composition containing a polypeptide, wherein with respect to the mammal the polypeptide includes a self C5 amino acid segment and a viral amino acid segment.

In another aspect, the invention features an isolated nucleic acid, wherein the isolated nucleic acid encodes a polypeptide for administration to a mammal, and wherein with respect to the mammal the polypeptide includes a self C5 amino acid segment and a non-self C5 amino acid segment.

The invention also features an isolated nucleic acid, wherein the isolated nucleic acid encodes a polypeptide for administration to a mammal, and wherein with respect to the mammal the polypeptide contains a self C5 amino acid segment and a non-self vertebrate amino acid segment.

In another aspect, the invention features an isolated nucleic acid, wherein the isolated nucleic acid encodes a polypeptide for administration to a mammal, wherein with respect to the mammal the polypeptide includes a self C5 amino acid segment and a non-self amino acid segment, and wherein the length of the non-self amino acid segment is less than 350 (e.g., less than 300, less than 250, or less than 200) amino acid residues.

In still another aspect, the invention features an isolated nucleic acid, wherein the isolated nucleic acid encodes a polypeptide for administration to a mammal, wherein with respect to the mammal the polypeptide contains a self C5 amino acid segment and a bacterial amino acid segment, and wherein the polypeptide lacks a factor Xa cleavage site between the C5 amino acid segment and the bacterial amino acid segment. The bacterial amino acid segment can be MBP.

In another aspect, the invention features an isolated nucleic acid, wherein the isolated nucleic acid encodes a polypeptide for administration to a mammal, and wherein with respect to the mammal the polypeptide includes a self C5 amino acid segment and a fungal amino acid segment.

The invention also features an isolated nucleic acid, wherein the isolated nucleic acid encodes a polypeptide for administration to a mammal, and wherein with respect to the mammal the polypeptide contains a self C5 amino acid segment and a viral amino acid segment.

The invention also features a host cell containing (1) an isolated nucleic acid, where the isolated nucleic acid encodes a polypeptide for administration to a mammal, wherein with respect to the mammal the polypeptide includes a C5 amino acid segment and a non-self C5 amino acid segment; (2) an isolated nucleic acid, where the isolated nucleic acid encodes a polypeptide for administration to a mammal, wherein with respect to the mammal the polypeptide includes a self C5 amino acid segment and a non-self vertebrate amino acid segment; (3) an isolated nucleic acid, where the isolated nucleic acid encodes a polypeptide for administration to a mammal, wherein with respect to the mammal the polypeptide includes a self C5 amino acid segment and a non-self amino acid segment, the length of the non-self amino acid segment being less than 350 (e.g., less than 300, less than 250, or less than 200) amino acid residues; (4) an isolated nucleic acid, where the isolated nucleic acid encodes a polypeptide for administration to a mammal, wherein with respect to the mammal the polypeptide includes a self C5 amino acid segment and a non-self bacterial amino acid segment; (5) an isolated nucleic acid, where the isolated nucleic acid encodes a polypeptide for administration to a mammal, wherein with respect to the mammal the polypeptide includes a self C5 amino acid segment and a non-self fungal amino acid segment; and/or (6) an isolated nucleic acid, where the isolated nucleic acid encodes a polypeptide for administration to a mammal, wherein with respect to the mammal the polypeptide includes a self C5 amino acid segment and a non-self viral amino acid segment. The host cell can express the polypeptide.

In yet another aspect, the invention features a composition for administration to a mammal. The composition can contain a polypeptide, wherein with respect to the mammal the polypeptide contains a self C5 amino acid segment and a non-self amino acid segment, and wherein the self C5 amino acid segment is at least 90 percent identical to a C5 sequence from the mammal.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following drawings and detailed description, and from the claims.

DESCRIPTION OF DRAWINGS

FIG. 1 is a depiction of a mouse pro-C5 DNA sequence (SEQ ID NO:1).

FIG. 2 is a depiction of the amino acid sequence of mouse pro-C5 including the signal peptide (SEQ ID NO:2).

FIG. 3 is a diagram depicting a nucleic acid vector designed to express a fusion polypeptide containing maltose binding protein (MBP) and mouse C5a.

FIG. 4 is the nucleic acid sequence of a MBP-C5a PCR product (SEQ ID NO:3).

FIG. 5 is the amino acid sequence of a MBP-C5a fusion polypeptide (SEQ ID NO:4).

FIG. 8 is a graph plotting the mean maximum arthritis score for collagen-induced arthritis in control mice and in mice vaccinated with a MBP-C5a fusion polypeptide. **, $p<0.01$.

DETAILED DESCRIPTION

Figure 3:
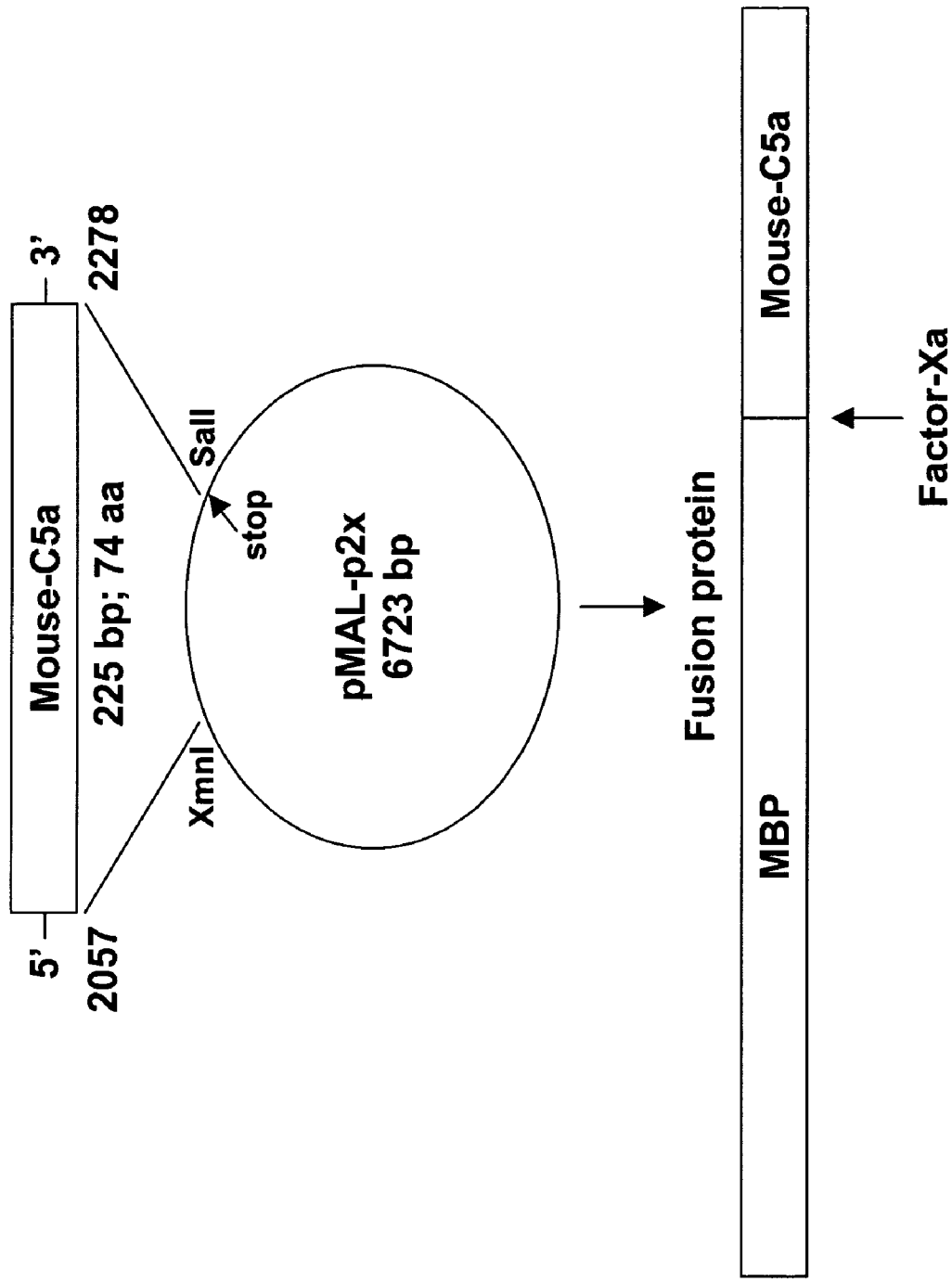

The invention provides methods and materials for treating inflammatory conditions. The term "inflammatory condition" as used herein refers to a disease, disease state, syndrome, or other condition resulting in inflammation. For example, rheumatoid arthritis and asthma are inflammatory conditions. Other examples of inflammatory conditions include, without limitation, sepsis, myocardial ischemia/reperfusion injury, adult respiratory distress syndrome, nephritis, graft rejection, inflammatory bowel disease, multiple sclerosis, arteriosclerosis, and vasculitis. The invention provides polypeptides, isolated nucleic acids, host cells, and methods for inducing an antibody response in a mammal against an antigen such as C5 or C5a. For example, the methods and materials described herein can be used to reduce the effects of C5a in a mammal by reducing the amount of total and/or receptor bound C5a.

Polypeptides

The invention provides polypeptides that can be used to treat an inflammatory condition. Such polypeptides can be immunogenic. An "immunogenic" polypeptide is any polypeptide that effectively induces an antibody response in a mammal. For example, an immunogenic polypeptide can be a polypeptide that effectively induces the production of an anti-self C5 antibody in a mammal.

Polypeptides of the invention can contain at least one amino acid segment that would be considered non-self to the particular mammal receiving the polypeptide. For example, a polypeptide that induces production of an anti-self C5 antibody can contain a self C5 amino acid segment and a non-self amino acid segment (e.g., a non-self C5 amino acid segment). The self C5 amino acid segment can confer the specificity of the anti-self C5 antibody response, and the non-self amino acid segment can enhance the immunogenicity of the polypeptide. The non-self amino acid segment (e.g., a non-self C5 amino acid segment) can contain at least two T cell epitopes. Alternatively, the non-self amino acid segment can stabilize an immunogenic polypeptide such that the specific anti-self C5 antibody response is induced. The self C5 amino acid segment of a polypeptide can be a portion of C5 that directly interacts with a C5a receptor. Examples of such self C5 amino acid segments include, without limitation, C5a or fragments of C5a. Additionally, the self C5 amino acid segment of a polypeptide can be a portion of C5 that indirectly influences the interaction of C5a with a C5a receptor. For example, a polypeptide containing the C5 convertase recognition sequence of C5 can induce the production of antibodies that bind to the C5 convertase recognition sequence of C5, thereby inhibiting the conversion of C5 to C5a by C5 convertase.

The term "amino acid segment" as used herein refers to a contiguous stretch of amino acids within a polypeptide. For example, the amino acid residues 30 to 40 within a 100 amino acid polypeptide would be considered an amino acid segment. An amino acid segment can be any length greater than eight amino acid residues (e.g., greater than about nine, ten, 15, 20, 25, 30, 40, 50, 75, 100, 150, 200, 500, 1000, or more amino acid residues). Thus, an amino acid segment can be C5, the entire C5a region of C5, or a portion of C5a. In some embodiments, an amino acid segment can have a length less than 1000 amino acid residues (e.g., less than 500, less than 400, less than 350, less than 300, less than 200, or less than 100 amino acid residues). In other embodiments, an amino acid segment can have a length from about 20 to about 200 amino acid residues (e.g., about 30 to about 180 amino acid residues, or about 40 to about 150 amino acid residues).

The term "self" as used herein with respect to an amino acid segment and a particular mammal generally refers to any amino acid segment that the particular mammal possesses endogenously. If an amino acid segment is derived from a member of one species and introduced into another member of the same species that endogenously possesses the amino acid segment, then that particular amino acid segment is considered a self amino acid segment. For example, a C5 amino acid segment derived from a mouse is a self C5 amino acid segment when introduced into that same mouse, a genetically identical mouse, or a non-genetically identical mouse that endogenously possesses the same amino acid segment.

The term "non-self" as used herein with respect to an amino acid segment and a particular mammal generally refers to any amino acid segment that the particular mammal does not possess endogenously. If an amino acid segment is derived from a member of a first species and introduced into a member of a second species that does not endogenously possess the amino acid segment, then that particular amino acid segment can be considered a non-self amino acid segment. For example, a C5 amino acid segment derived from a mouse can be considered a non-self C5 amino acid segment when introduced into a human. In another example, if a polypeptide contains a C5a amino acid segment from a mouse and a C5b amino acid segment from a human, and that polypeptide is introduced into a mouse, then the C5a amino acid segment can be considered a self C5a amino acid segment and the C5b amino acid segment can be considered a non-self C5b amino acid segment. Alternatively, if the same polypeptide is introduced into a human, the C5a amino acid segment can be considered a non-self C5a amino acid segment and the C5b amino acid segment can be considered a self C5b amino acid segment. If an amino acid segment from one member of a species is considered polymorphic to another member of the same species, then that amino acid segment can be considered a non-self amino acid segment to a member of the species not possessing that polymorphism. For example, if a C5 amino acid segment from a human having one type of polymorphism in the amino acid segment is introduced into a second human that does not have that particular type of polymorphism, the C5 amino acid segment can be considered a non-self amino acid segment to the second human. It also will be understood that cryptic T cell epitopes (i.e., self peptides that under normal conditions are not expressed on MHC molecules to the level required for recognition by T cells) can be considered non-self.

The non-self and self amino acid segments can be from either the same or different naturally-occurring polypeptides. For example, if a polypeptide contains a self amino acid segment from human C5, then the non-self amino acid segment can be from either the same type of polypeptide (e.g., rat C5) or a different type of polypeptide (e.g., rat albumin). In another example, a polypeptide can contain a self C5a amino acid segment and one or more non-self T cell epitopes provided by MBP. Further, an amino acid segment can be from any type of polypeptide including, without limitation, a bacterial polypeptide (e.g., MBP), a fungal polypeptide, a viral polypeptide, or a mammalian polypeptide.

The self segment or segments of the polypeptides provided herein typically are at least 90 percent identical (e.g., at least 91, 92, 93, 94, 95, 96, 97, 98, or 99 percent identical) to a sequence from a polypeptide found in the mammal to which the polypeptide will be administered. In some embodiments, the self segment can be 100 percent identical to a sequence from a polypeptide found in the mammal to which the polypeptide will be administered. The invention thus provides polypeptides that contain an amino acid segment having (1) a length, and (2) a percent identity to a reference amino acid sequence (e.g., an amino acid sequence from a particular mammal) over that length. The invention also provides isolated nucleic acid molecules that contain a nucleic acid sequence encoding a polypeptide that contains an amino acid segment having (1) a length, and (2) a percent identity to a mammal's amino acid sequence over that length. Typically, the mammalian amino acid or nucleic acid sequence is a referred to as a reference sequence, and the amino acid or nucleic acid sequence being compared to the mammalian sequence is referred to as the target sequence. For example, a mammal's sequence can be the reference sequence having the sequence set forth in SEQ ID NO:2.

A length and percent identity over that length for any amino acid or nucleic acid sequence is determined as follows. First, an amino acid or nucleic acid sequence is compared to an amino acid or nucleic acid sequence from the mammal to which it will be administered using the BLAST 2 Sequences (B12seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast"), the U.S. government's National Center for Biotechnology Information web site (World Wide Web at "ncbi" dot "nlm" dot "nih" dot "gov"), or the State University of New York at Old Westbury Library (QH 497.m6714). Instructions explaining how to use the Bl2seq program can be found in the readme file accompanying BLASTZ.

B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default settings. For example, the following command can be used to generate an output file containing a comparison between two sequences: C:\B12seq -i c:\seq1.txt -j c:\seq2.txt -p blastn -o c:\output-.txt -q -1 -r 2. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default settings. For example, the following command can be used to generate an output file containing a comparison between two amino acid sequences: C:\B12seq -i c:\seq1.txt -j c:\seq2.txt -p blastp -o c:output.txt. If the target sequence shares homology with any portion of the mammalian sequence, then the designated output file will present those regions of homology as aligned sequences. If the target sequence does not share homology with any portion of the mammalian sequence, then the designated output file will not present aligned sequences.

Once aligned, a length is determined by counting the number of consecutive nucleotides or amino acid residues from the target sequence presented in alignment with sequence from the mammalian sequence. A matched position is any position where an identical nucleotide or amino acid residue is presented in both the target and mammalian sequence. Gaps presented in the target sequence are not counted since gaps are not nucleotides or amino acid residues.

Likewise, gaps presented in the mammalian sequence are not counted since target sequence nucleotides or amino acid residues are counted, not nucleotides or amino acid residues from the mammalian sequence.

The percent identity over a determined length is determined by counting the number of matched positions over that length and dividing that number by the length followed by multiplying the resulting value by 100. For example, if (1) a 300 amino acid target sequence is compared to a reference sequence, (2) the B12seq program presents 200 consecutive amino acids from the target sequence aligned with a region of the reference sequence, and (3) the number of matches over those 200 aligned amino acids is 180, then that 300 amino acid target sequence contains an amino acid segment that has a length of 200 and a percent identity over that length of 90 (i.e., 180÷200*100=90).

It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It is also noted that the length value will always be an integer.

The non-self segment or segments of the polypeptides provided herein typically are less than 95 percent identical (e.g., less than 94, 93, 92, 91, 90, 85, 80, 75, 70, 65, 60, 55, or 50 percent identical) to a sequence from a polypeptide found in the mammal to which the polypeptide will be administered.

Any method can be used to make a polypeptide including, for example, expression by prokaryotic systems, expression by eukaryotic systems, and chemical synthesis techniques. Any method can be used to purify a polypeptide including, without limitation, fractionation, centrifugation, and chromatography. For example, polypeptides containing maltose binding protein (MBP) can be purified using amylose affinity chromatography.

Nucleic Acids

The invention provides isolated nucleic acids encoding polypeptides such as those described herein (e.g., polypeptides containing self and non-self amino acid segments). For example, a nucleic acid of the invention can encode a polypeptide having the amino acid sequence set forth in SEQ ID NO:2. Alternatively, a nucleic acid of the invention can encode a polypeptide having an amino acid sequence that contains a portion of the sequence set forth in SEQ ID NO:2. In another embodiment, a nucleic acid provided herein can encode a polypeptide having the amino acid sequence set forth in SEQ ID NO:4. An isolated nucleic acid also can encode a polypeptide containing a self C5 amino acid segment and a non-self amino acid segment (e.g., a non-self C5 amino acid segment, or a non-self vertebrate, bacterial, fungal, or viral amino acid segment). The self segment encoded by the isolated nucleic acid can contain an amino acid segment (e.g., a C5 amino acid segment) with at least 90 percent identity (e.g., at least 91, 92, 93, 94, 95, 96, 97, 98, or 99 percent identity, or 100 percent identity) to an amino acid sequence from a polypeptide found in the mammal to which the polypeptide will be administered. The non-self segment encoded by the isolated nucleic acid can contain an amino acid segment with less than 95 percent identity (e.g., less than 94, 93, 92, 91, 90, 85, 80, 75, 70, 65, 60, 55, or 50 percent identity) to an amino acid sequence from a polypeptide found in the mammal to which the polypeptide will be administered.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to a nucleic acid refers to a naturally-occurring nucleic acid that is not immediately contiguous with one or both of the sequences with which it is immediately contiguous (one at the 5' end and one at the 3' end) in the naturally-occurring genome of the organism from which it is derived. For example, an isolated nucleic acid can be, without limitation, a recombinant DNA of any length, provided one of the nucleic acid sequences normally found immediately flanking that recombinant DNA in a naturally-occurring genome is removed or absent. Thus, an isolated nucleic acid includes, without limitation, a recombinant DNA that is independent of other sequences (e.g., a cDNA or a genomic DNA fragment produced by PCR or restriction endonuclease treatment), as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA that is part of a hybrid or fusion nucleic acid sequence.

The term "isolated" as used herein with reference to a nucleic acid also includes any non-naturally-occurring nucleic acid since non-naturally-occurring nucleic acid sequences are not found in nature and do not have immediately contiguous sequences in a naturally occurring genome. For example, a non-naturally-occurring nucleic acid such as an engineered nucleic acid is considered to be an isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid that is part of a hybrid or fusion nucleic acid sequence.

A nucleic acid existing among hundreds to millions of other nucleic acids within, for example, cDNA or genomic libraries, or gel slices containing a genomic DNA restriction digest is not to be considered an isolated nucleic acid.

The term "exogenous" as used herein with reference to a nucleic acid and a particular cell refers to any nucleic acid that does not originate from that particular cell as found in nature. Thus, any non-naturally-occurring nucleic acid is considered to be exogenous to a cell once introduced into the cell. It is important to note that a non-naturally-occurring nucleic acid can contain nucleic acid sequences or fragments of nucleic acid sequences that are found in nature, provided the nucleic acid as a whole does not exist in nature. For example, a nucleic acid containing a genomic DNA sequence within an expression vector is a non-naturally-occurring nucleic acid, and thus is exogenous to a cell once introduced into the cell since that nucleic acid as a whole (genomic DNA plus vector DNA) does not exist in nature. Thus, any vector, autonomously replicating plasmid, or virus (e.g., a retrovirus, adenovirus, or herpes virus) that as a whole does not exist in nature is considered to be a non-naturally-occurring nucleic acid. It follows that genomic DNA fragments produced by PCR or restriction endonuclease treatment as well as cDNAs are considered to be non-naturally-occurring nucleic acids since they exist as separate molecules not found in nature. It also follows that any nucleic acid containing a promoter sequence and polypeptide-encoding sequence (e.g., cDNA or genomic DNA) in an arrangement not found in nature is a non-naturally-occurring nucleic acid.

A nucleic acid that is naturally occurring can be exogenous to a particular cell. For example, an entire chromosome isolated from a cell of person X is an exogenous nucleic acid with respect to a cell of person Y once that chromosome is introduced into Y's cell.

Isolated nucleic acids can be obtained using any method including, without limitation, common molecular cloning and chemical nucleic acid synthesis techniques. For example, PCR can be used to obtain an isolated nucleic acid containing a nucleic acid sequence having similarity to the sequence set forth in SEQ ID NO:1. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, or cDNA, as well as from bacteriophage sequences, plasmid sequences, viral sequences, and the like. When using RNA as a source of template, reverse transcriptase can be used to synthesize complimentary DNA strands.

Isolated nucleic acids also can be obtained by mutagenesis. For example, an isolated nucleic acid containing a sequence set forth in SEQ ID NO:1 can be mutated using common molecular cloning techniques (e.g., site-directed mutagenesis). Possible mutations include, without limitation, deletions, insertions, and substitutions, as well as combinations of deletions, insertions, and substitutions.

In addition, nucleic acid and amino acid databases (e.g., GenBank®) can be used to obtain an isolated nucleic acid. For example, any nucleic acid sequence having some homology to a sequence set forth in SEQ ID NO:1, or any amino acid sequence having some homology to a sequence set forth in SEQ ID NO:2 can be used as a query to search GenBank®.

Further, nucleic acid hybridization techniques can be used to obtain an isolated nucleic acid. Briefly, any nucleic acid having some homology to a sequence set forth in SEQ ID NO:1 can be used as a probe to identify a similar nucleic acid by hybridization under conditions of moderate to high stringency. Once identified, the nucleic acid then can be purified, sequenced, and analyzed to determine whether it is within the scope of the invention as described herein.

Hybridization can be done by Southern or Northern analysis to identify a DNA or RNA sequence, respectively, which hybridizes to a probe. The probe can be labeled with biotin, digoxygenin, an enzyme, or a radioisotope such as $^{32}P$. The DNA or RNA to be analyzed can be electrophoretically separated on an agarose or polyacrylamide gel, transferred to nitrocellulose, nylon, or another suitable membrane, and hybridized with the probe using standard techniques well known in the art such as those described in sections 7.39-7.52 of Sambrook et al., (1989) Molecular Cloning, second edition, Cold Spring harbor Laboratory, Plainview, N.Y.

Further, any method can be used to direct the transcription or translation of a particular isolated nucleic acid encoding a polypeptide. Such methods include, without limitation, constructing a nucleic acid such that a regulatory element promotes expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like.

Host Cells

The invention provides host cells containing at least one isolated nucleic acid described herein. Such cells can be prokaryotic cells or eukaryotic cells. It is noted that cells containing an isolated nucleic acid within the scope of the invention are not required to express a polypeptide. In addition, the isolated nucleic acid can be integrated into the genome of the cell or maintained in an episomal state. Thus, host cells can be stably or transiently transfected with a construct containing an isolated nucleic acid of the invention.

The host cells provided herein can contain an exogenous nucleic acid that encodes a polypeptide. For example, cells can contain a nucleic acid encoding a self C5 amino acid segment and a non-self amino acid segment. In addition, the host cells can express the encoded polypeptide.

Any method can be used to introduce an isolated nucleic acid into a cell in vivo or in vitro. For example, calcium phosphate precipitation, electroporation, heat shock, lipofection, microinjection, and viral-mediated nucleic acid transfer are common methods that can be used to introduce an isolated nucleic acid into a cell. In addition, naked DNA can be delivered directly to cells in vivo as describe elsewhere (see, e.g., U.S. Pat. Nos. 5,580,859 and 5,589,466, and continuations thereof). Further, isolated nucleic acids can be introduced into cells by generating transgenic animals.

Transgenic animals can be aquatic animals (such as fish, sharks, dolphins, and the like), farm animals (such as pigs, goats, sheep, cows, horses, rabbits, and the like), rodents (such as mice, guinea pigs, and rats), non-human primates (such as baboon, monkeys, and chimpanzees), and domestic animals (such as dogs and cats). Several techniques known in the art can be used to introduce isolated nucleic acids into animals to produce the founder lines of transgenic animals. Such techniques include, without limitation, pronuclear microinjection (U.S. Pat. No. 4,873,191); retrovirus mediated gene transfer into germ lines (Van der Putten et al., *Proc. Natl. Acad. Sci., USA*, 82:6148 (1985)); gene transfection into embryonic stem cells (Gossler et al., *Proc Natl. Acad. Sci. USA* 83:9065-9069 (1986)); gene targeting into embryonic stem cells (Thompson et al., *Cell*, 56:313 (1989)); nuclear transfer of somatic nuclei (Schnieke et al., *Science* 278:2130-2133 (1997)); and electroporation of embryos (Lo *Mol. Cell. Biol.*, 3:1803-1814 (1983)). Once obtained, transgenic animals can be replicated using traditional breeding or animal cloning.

Any method can be used to identify cells containing an isolated nucleic acid of the invention. Such methods include, without limitation, PCR and nucleic acid hybridization techniques such as Northern and Southern analysis. In some cases, immunohistochemistry and biochemical techniques can be used to determine if a cell contains a particular isolated nucleic acid by detecting the expression of a polypeptide encoded by that particular nucleic acid.

Methods for Treating Inflammatory Conditions

The polypeptides provided herein can be used in the manufacture of a medicament or composition for treating inflammatory conditions. Thus, the invention provides methods for treating inflammatory conditions. Such methods include, without limitation, administering a composition to a mammal. A composition can contain a polypeptide that acts as an antigen against which an immune response is desired. Further, a composition can contain more than one polypeptide, or any combination of different polypeptides. For example, a composition can contain both viral polypeptides and mammalian polypeptides. It is noted that each polypeptide in a composition can have an identical amino acid sequence. In addition, the polypeptides in a composition can contain different amino acid segments, each of which can act as a defined antigenic unit against which an immune response is desired. Thus, the polypeptides in a composition can contain different amino acid segments that correspond to any region from a polypeptide including, without limitation, receptor binding regions, ligand binding regions, enzyme active sites, enzyme cleavage sites of polypeptide substrates, antigen-binding regions of antibodies, and epitopes recognized by antibodies. For example, the polypeptides in a composition can encompass three different amino acid segments, each of which corresponds to the C5 convertase recognition sequence of C5. In addition, different or identical amino acid segments can be in tandem or dispersed throughout the same polypeptide. Typically, the administration of a polypeptide results in the formation of antibodies having specificity for an epitope or combination of epitopes formed by the amino acid segments within one or more of the polypeptides in the composition.

A composition can contain an isolated nucleic acid designed to express a particular polypeptide when introduced into a host cell. For example, an isolated nucleic acid can be designed to encode a polypeptide having a self C5a amino acid segment and one or more than one non-self T cell epitope. Once constructed, the isolated nucleic acid can be introduced into a host cell such that the encoded polypeptide is expressed. Any host cell can be used including, without limitation, prokaryotic cells (e.g., bacteria) and eukaryotic cells (e.g., human cells). Once produced, the polypeptide can be purified and used to vaccinate a mammal. Alternatively, a composition containing an isolated nucleic acid designed to express a particular polypeptide can be administered to a mammal such that the polypeptide is expressed in vivo.

A composition can be made by combining any of the polypeptides (e.g., immunogenic polypeptides) or isolated nucleic acids (e.g., nucleic acids encoding immunogenic polypeptides) provided herein with a pharmaceutically acceptable carrier. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters, for example. Aqueous carriers include, without limitation, water, alcohol, saline, and buffered solutions. Preservatives, flavorings, and other additives such as, for example, antimicrobials, antioxidants, chelating agents, inert gases, and the like also may be present. It will be appreciated that any material described herein that is to be administered to a mammal can contain one or more pharmaceutically acceptable carriers.

A composition also can include an adjuvant. An "adjuvant" is an immunological compound that can enhance an immune response against a particular antigen such as a polypeptide. Adjuvants such as, for example, alum and other aluminum-based compounds (e.g., $Al_2O_3$) can be combined with a polypeptide containing a self amino acid segment (e.g., a self C5 amino acid segment) to form a composition that elicits an anti-self response when administered to a mammal. Aluminum-based compounds can be obtained from various commercial suppliers. For example, REHYDRAGEL® adjuvants can be obtained from Reheis Inc. (Berkeley Heights, N.J.). REHYDRAGEL® adjuvants are based on crystalline aluminum oxyhydroxide, and are hydrated gels containing crystalline particles with a large surface area (about 525 $m^2/g$). Their $Al_2O_3$ content typically ranges from about 2 percent to about 10 percent. Rehydragel LG, for example, has an $Al_2O_3$ content of about 6 percent, and flows readily upon slight agitation. Rehydragel LG also has a protein binding capacity of 1.58 (i.e., 1.58 mg of bovine serum albumin bound per 1 mg of $Al_2O_3$), a sodium content of 0.02 percent, a chloride content of 0.28 percent, undetectable sulphate, an arsenic level less than 3 ppm, a heavy metal content less than 15 ppm, a pH of 6.5, and a viscosity of 1090 cp. Rehydragel LG can be combined with a polypeptide solution (e.g., a polypeptide in PBS) to yield Al(OH)$_3$. In addition, ALHYDROGEL™, an aluminum hydroxy gel adjuvant, (Alhydrogel 1.3%, Alhydrogel 2.0%, or Alhydrogel "85") obtained from Brenntag Stinnes Logistics can be used.

In addition, MN51 can be combined with the polypeptides provided herein to form a composition that elicits an anti-self response when administered to a mammal. MN51 (MONTANIDE® Incomplete SEPPIC Adjuvant (ISA) 51) as well as MN720 are available from Seppic (Paris, France). MN51 contains mannide oleate (MONTANIDE® 80, also known as anhydro mannitol octadecenoate) in mineral oil solution (Drakeol 6 VR). MONTANIDE® 80 is a limpid liquid with a maximum acid value of 1, a saponification value of 164-172, a hydroxyl value of 89-100, an iodine value of 67-75, a maximum peroxide value of 2, a heavy metal value less than 20 ppm, a maximum water content of 0.35%, a maximum color value of 9, and a viscosity at 25° C. of about 300 mPas. MONTANIDE® associated with oil (e.g., mineral oil, vegetable oil, squalane, squalene, or esters) is known as MONTANIDE® ISA. Drakeol 6 VR is a pharmaceutical grade mineral oil. Drakeol 6 VR contains no unsaturated or aromatic hydrocarbons, and has an A.P.I. gravity of 36.2-36.8, a specific gravity at 25° C. of 0.834-0.838, a viscosity at 100° F. of 59-61 SSU or 10.0-10.6 centistokes, a refractive index at 25° C. of 1.458-1.463, a better than minimum acid test, is negative for fluorescence at 360 nm, is negative for visible suspended matter, has an ASTM pour test value of 0-15° F., has a minimum ASTM flash point of 295° F., and complies with all RN requirements for light mineral oil and ultraviolet absorption. MN51 contains about 8 to 12 percent anhydro mannitol octadecenoate and about 88 to 92 percent mineral oil. MN51 is a clear yellow liquid having a maximum acid value of 0.5, a saponification value of 16-20, a hydroxyl value of 9-13, a maximum peroxide value of 2, an iodine value of 5-9, a maximum water content of 0.5 percent, a refractive index at 25° C. between 1.455 and 1.465, a density at 20° C. of about 0.85, and a viscosity at 20° C. of about 50 mPas. The conductivity of a 50:50 mixture of MN51 and saline is less than 10 $\mu$Scm$^{-1}$.

Other adjuvants include immuno-stimulating complexes (ISCOMs) that can contain such components as cholesterol and saponins. ISCOM matrices can be prepared and conjugated to Cu$^{2+}$ using methods such as those described herein. Adjuvants such as FCA, FIA, MN51, MN720, and Al(OH)$_3$ are commercially available from companies such as Seppic, Difco Laboratories (Detroit, Mich.), and Superfos Biosector A/S (Vedbeak, Demark).

In some embodiments, a composition also can contain one or more additional immunostimulatory components. These include, without limitation, muramyldipeptide (e.g., N-acetylmuramyl-L-alanyl-D-isoglutamine; MDP), monophosphoryl-lipid A (MPL), and formyl-methionine containing tripeptides such as N-formyl-Met-Leu-Phe. Such compounds are commercially available from Sigma Chemical Co. (St. Louis, Mo.) and RIBI ImmunoChem Research, Inc. (Hamilton, Mont.), for example.

The compositions provided herein can contain any ratio of adjuvant to polypeptide. The adjuvant:antigen ratio can be 50:50 (vol:vol), for example. Alternatively, the adjuvant:antigen ratio can be, without limitation, 90:10, 80:20, 70:30, 64:36, 60:40, 55:45, 40:60, 30:70, 20:80, or 90:10.

An effective amount of any composition provided herein can be administered to a host. The term "effective" as used herein refers to any amount that induces a desired immune response while not inducing significant toxicity in the host. Such an amount can be determined by assessing a host's immune response after administration of a known amount of a particular composition. In addition, the level of toxicity, if any, can be determined by assessing a host's clinical symptoms before and after administering a known amount of a particular composition. It is noted that the effective amount of a particular composition administered to a host can be adjusted according to a desired outcome as well as the host's response and level of toxicity. Significant toxicity can vary for each particular host and depends on multiple factors including, without limitation, the host's disease state, age, and tolerance to pain.

In addition, any composition described herein can be administered to any part of the host's body. A composition can be delivered to, without limitation, the joints, nasal mucosa, blood, lungs, intestines, muscle tissues, skin, or peritoneal cavity of a mammal. In addition, a composition can be administered by intravenous, intraperitoneal, intramuscular, subcutaneous, intrathecal, or intradermal injection, by oral or nasal administration, by inhalation, or by gradual perfusion over time. In a further example, an aerosol preparation of a composition can be given to a host by inhalation. The duration of treatment with any composition provided herein can be any length of time from as short as one day to as long as the life span of the host (e.g., many years). For example, a polypeptide can be administered once a month for three months or once a year for a period of ten years. It is also noted that the frequency of treatment can be variable. For example, a polypeptide can be administered once (or twice, three times, etc.) daily, weekly, monthly, or yearly.

Any method can be used to determine if a particular immune response is induced. For example, antibody responses against particular antigens can be determined using an immunological assay (e.g., an ELISA). In such an assay, the wells of a microtiter plate can be coated with C5 and incubated with serum from a mammal treated with a composition designed to produce anti-C5 antibodies in that mammal, and the presence or absence of anti-C5 antibodies can be determined using a labeled anti-rat IgG. In addition, clinical methods that can assess the degree of a particular disease state can be used to determine if a desired immune response is induced. For example, a reduction in inflammation can indicate a desired immune response in a patient treated with a composition designed to produce anti-C5 antibodies. To support an indication of a desired immune response, anti-C5 antibody levels in a blood sample from such a patient can be measured using the ELISA technique described above.

Articles of Manufacture

The invention also provides articles of manufacture that can include polypeptides and compositions provided herein. Components and methods for producing articles of manufacture are well known. An article of manufacture can include, for example, one or more polypeptides that induce production of an anti-self C5 antibody (e.g., one or more polypeptides containing a self C5 amino acid segment and a non-self amino acid segment such as a non-self C5 amino acid segment). In addition, an article of manufacture further may include, for example, buffers or other control reagents for treating or monitoring an inflammatory condition. In some embodiments, such articles of manufacture can include a label or instructions indicating that the polypeptides contained therein are effective for treating an inflammatory condition.

The invention will be further described in the following examples, which do not limit the scope of the invention described in the claims.

EXAMPLES

Example 1

Production and Purification of a Mouse C5a Polypeptide

A mouse pro-C5 DNA sequence (SEQ ID NO:1) is shown in FIG. 1, and the amino acid sequence of mouse pro-C5 including the signal peptide (SEQ ID NO:2) is shown in FIG. 2. The coding region for mouse C5a was isolated by PCR amplification from a total mouse liver cDNA library. The PCR fragment was ligated into the bacterial expression vector pMAL-p2x (FIG. 3; New England Biolabs, Beverly, Mass.), adjacent to a sequence encoding a portion of maltose binding protein (MBP). The coding region for the MBP-C5a fusion polypeptide was then amplified from this vector by PCR. To facilitate eventual purification of the fusion polypeptide, the 5' PCR primer also encoded six histidine residues. In addition, the 5' primer contained an EcoRI site, and the 3' primer contained a SalI site for cloning purposes. The PCR product (sequence shown in FIG. 4) was transferred into a mammalian expression vector, the episomally maintained pCEP-Pu2, which contains a signal sequence from a immunoglobulin variable region. The SalI site of the PCR product was ligated into the XhoI site of the pCEP-Pu2 vector, resulting in destruction of both sites. The nucleotide sequence of the PCR product encoding the fusion polypeptide is set forth in SEQ ID NO:3, and the amino acid sequence of the fusion polypeptide is set forth in SEQ ID NO:4.

Example 2

Expression and Purification of MBP-C5a From Mammalian Cells

The pCEP-Pu2 construct containing the 6His-MBP-C5a fusion polypeptide was transfected into 293-EBNA cells for over-expression and purification of the secreted fusion polypeptide. Mammalian EBNA-293 cells were transfected by lipofection and cultured in Dulbecco's Modified Eagle Medium (DMEM) supplemented with 5% fetal calf serum, 0.5 µg/ml puromycin, 50 µg/ml gentamicin, and 100 µg/ml geneticin. Growing cells were expanded, and conditioned media were collected every 4-5 days. Cells and debris were removed by centrifugation.

The fusion polypeptide contained six histidine residues to enable purification using Ni-NTA agarose. A 0.75 ml aliquot of Ni-NTA agarose slurry (QIAGEN GmbH, Germany) containing~0.35 ml beads in 20% ethanol was added per 500 ml of conditioned media. After overnight incubation at 4° C. on a shaker, the Ni-NTA agarose was pelleted by centrifugation for 10 minutes at about 2000 g and transferred to columns. The beads were washed with PBS, pH 7.4, in the presence of 1 M NaCl and 0.1% Tween-20, and eluted with 100 mM imidazole (Merck, Germany) in 20 mM Tris, pH 8.0, with 0.1 M NaCl, according to the manufacturer's instructions. Polypeptide-containing fractions were pooled and dialyzed against PBS, pH 7.4, using a membrane with a molecular weight cut-off of 12,000-14,000 Da (Spectra/Por Membranes, Spectrum Laboratories, Inc., Rancho Dominguez, Calif.). If necessary, samples were concentrated using a Macrosep 10K centrifugal device (PALL Gelman Laboratory). The final polypeptide concentration was estimated with Bradford assay (BIO-RAD Protein Assay, Bio-Rad Laboratories, Hercules, Calif.). The cells produced 6His-MBP-C5a fusion polypeptide at a level of about 2 mg/liter. A Rainbow protein molecular weight marker (Amersham International, Buckinghamshire, England) was used for size estimation. The polypeptide migrated at the expected size of 53 kD. The amino acid sequence of the fusion polypeptide is shown in FIG. 5.

Example 3

Effect of MBP-C5a on Murine Collagen-induced Arthritis

Purified 6His-MBP-C5a polypeptide in PBS was combined with Complete Freund's Adjuvant (CFA) or Incomplete Freund's Adjuvant (IFA) in a 1:1 ratio immediately before use. The solution was repeatedly drawn up and down in a Hamilton syringe (Hamilton Corp., Reno, Nev.) equipped with an 18G needle, and was mixed until a white emulsion with rheological characteristics similar to an ointment was formed. A 23G needle was placed on the syringe for administration of the mixture. A control mixture containing equal volumes of PBS and CFA or IFA also was prepared.

Twelve week-old male QB (Balb/c X B10.Q) F1 mice were divided into two groups of 14 or 16 animals each, and were subcutaneously injected between the scapulae on day-21 with either 100 µg of MBP-C5a emulsified in CFA or with the control mixture. Blood samples also were taken on day-21, and the sera were stored at -20° C. Animals received booster injections of either 50 µg of MBP-C5a in IFA or the control mixture on day-3 and on day 28. Injections typically were administered in a volume of 100 to 200 µL.

To induce arthritis, mice were intradermally injected at the root of the tail on day 0 with 100 µg of pepsin-digested CII emulsified 1:1 in CFA. Arthritis was expected to develop between days 28 and 56. Animals received a booster injection of CII emulsified in IFA on day 35, and blood samples were taken on day 35. Animals were examined at least three times weekly from day 14 until day 90, when the experiment was ended. Animals were scored blindly using a scoring system based on the number of inflamed joints in each paw. Inflammation was defined by swelling and redness. In this scoring system, each inflamed toe or knuckle was given one point, whereas an inflamed wrist or ankle was given five points. This resulted in a score of 0-15 for each paw (5 toes+5 knuckles+1 wrist/ankle), and 0-60 for each mouse. The experiment was terminated on day 90 or when it was deemed appropriate based on development of arthritis. No mice exhibited signs of abnormal fur status, stereotypic or behavioral changes, infection, or other severe or unexpected side effects apart from symptoms normally occurring in connection with the expected arthritis disease. Animals were anesthetized with enfluran (Forene®)/oxygen, and blood was obtained by reorbital puncture. Serum was collected and stored at −20° C. Sera collected on days -21, 35, and at the end of the study were evaluated for anti-CII and anti-C5a antibody levels using an ELISA method.

Figure 6:
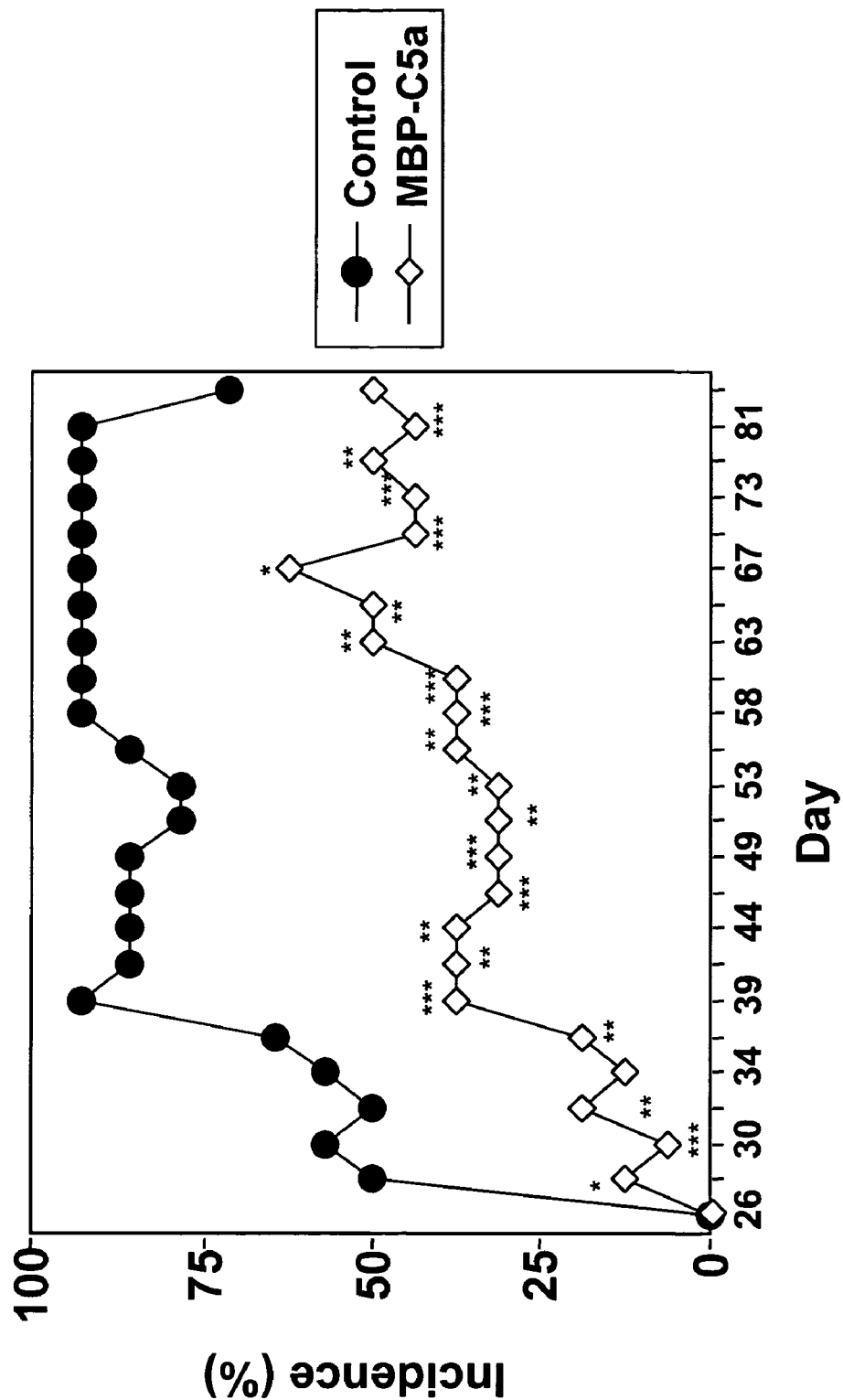
FIG. 6 is a graph plotting the incidence of collagen-induced arthritis in control mice (open diamonds) and in mice vaccinated with a MBP-C5a fusion polypeptide (filled circles). *, $p<0.05$;, $p<0.01$; *, $p<0.005$.

The Mann-Whitney test was used to analyze the scoring data, and areas under the curve and chi-square values were used to analyze the significance of the incidence of arthritis. On day 28 after the first collagen treatment, seven of the 14 mice in the control group (50%) displayed inflammation, while only two of the 16 mice (12.5%) pre-treated with MBP-C5a displayed inflammation (FIG. 6). These data resulted in a chi-square P value of 0.025. The cumulative incidence of inflammation (as of day 67) was 14 out of 14 in the control group and 11 out of 16 in the group pretreated with MBP-C5a (P=0.022). Thus, the incidence of collagen-induced arthritis was significantly different between the two groups.

Figure 7:
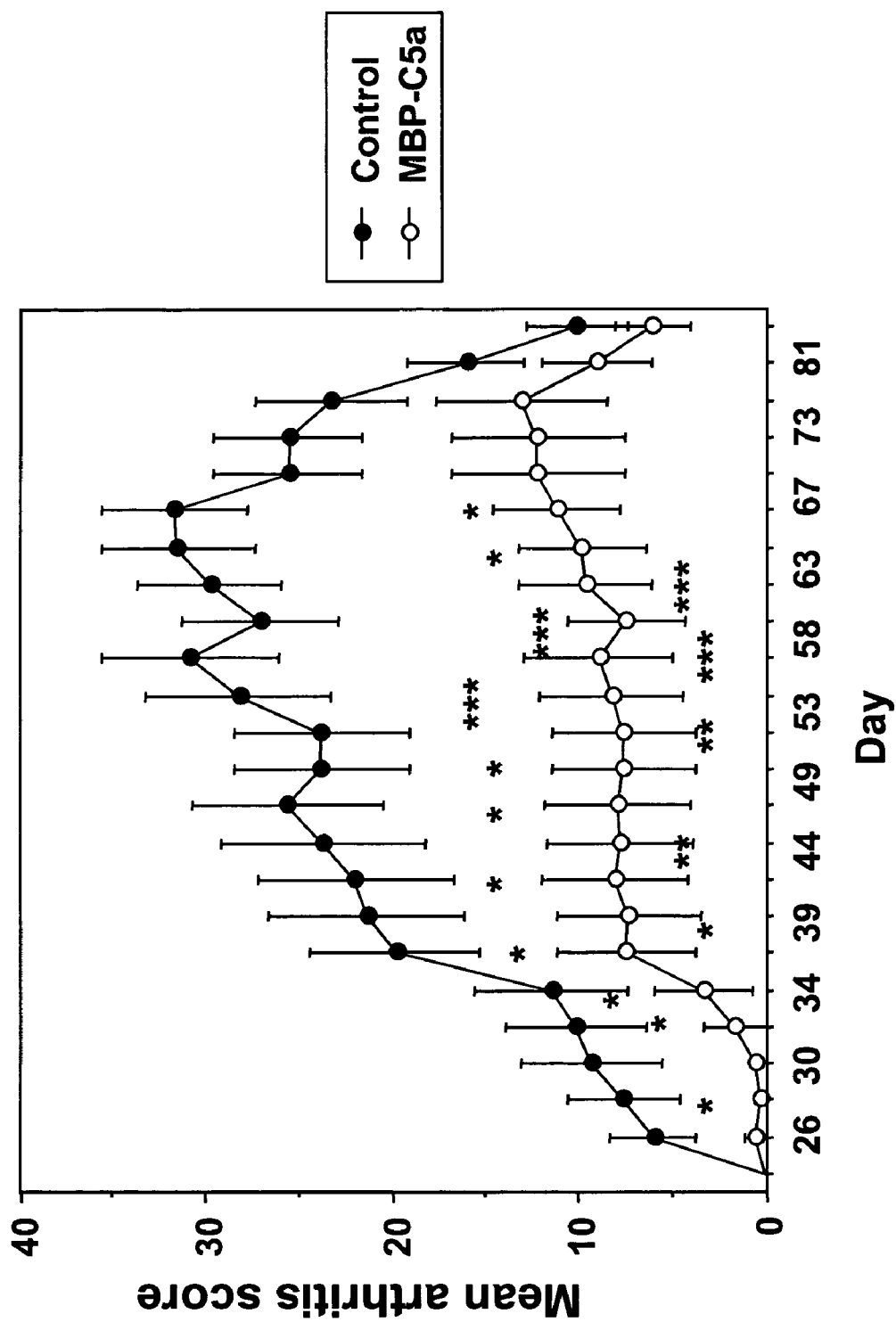
FIG. 7 is a graph plotting the mean arthritis score for collagen-induced arthritis in control mice (open circles) and in mice vaccinated with a MBP-C5a fusion polypeptide (filled circles). *, $p<0.05$; , $p<0.01$; *, $p<0.005$.
Figure 9:
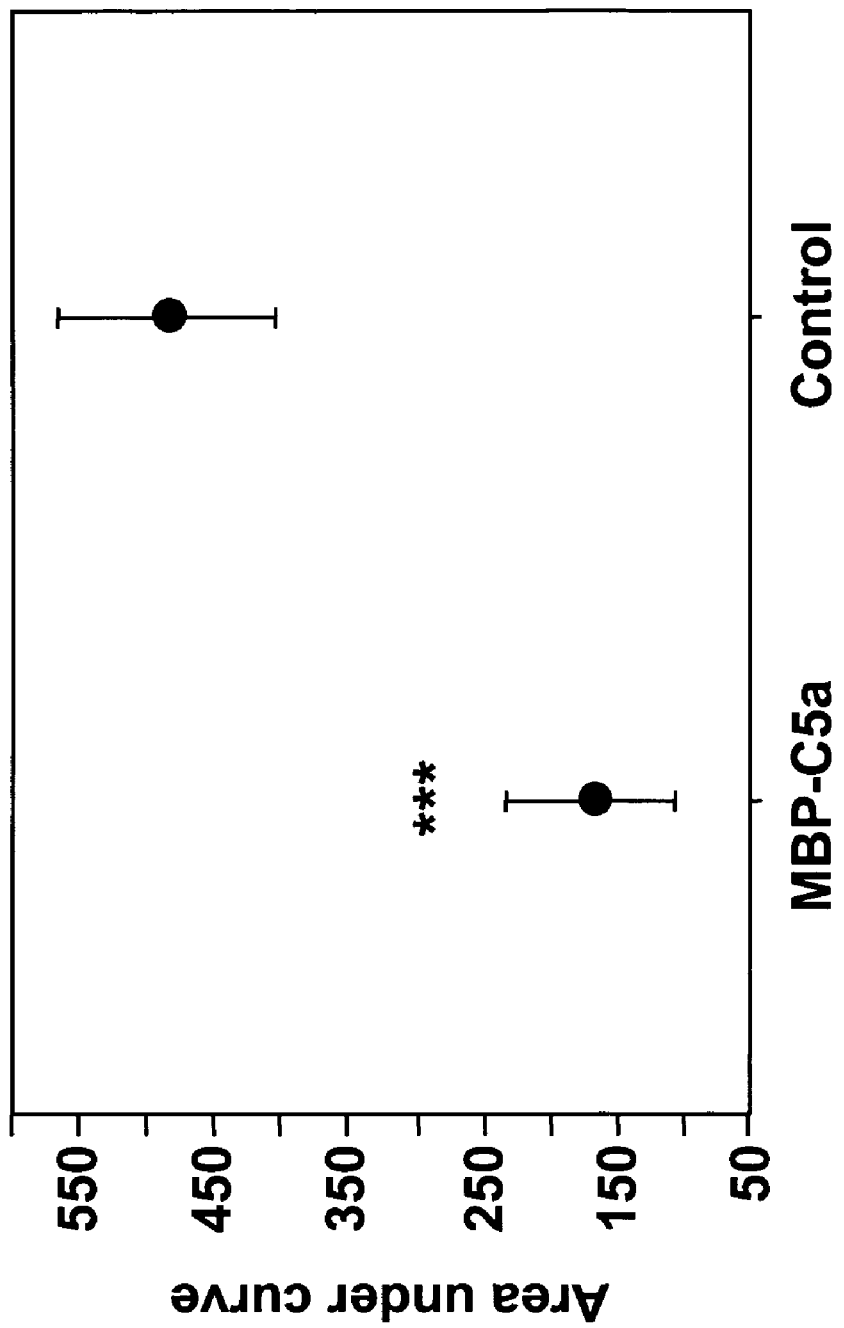
FIG. 9 is a graph plotting the area under the curve for arthritis score data obtained from mice injected with collagen and then treated with PBC (control) or a MBP-C5a fusion polypeptide. ***, $p<0.005$.

A mean arthritis score based on the amount of inflammation was plotted for each group between days 1 and 90 (FIG. 7). The maximum one-mouse score for each group was 60. At the end of the study, the maximum severity resulted in a mean value of 38.6 in the control group and 19.0 in the group pretreated with MBP-C5a (P=0.0085; FIG. 8). The area under the curve resulted in a mean value of 485.9 in the control group and 168.9 in the group pretreated with MBP-C5a (P=0.0012; FIG. 9). These results demonstrated that treatment with the MBP-C5a fusion polypeptide resulted in decreases in the incidence and severity of collagen-induced arthritis in these animals.

Example 4

Effect of MBP-C5a on Chronic Collagen-induced Arthritis in QB-BC Mice

Purified MBP-C5a polypeptide in PBS was combined with CFA or IFA as described above. A control mixture containing equal volumes of PBS and CFA or IFA also was prepared.

Eight- to ten-week-old male and female QB-BC (B10.Q (Balb/c X B10.Q)) mice were intradermally injected at the root of the tail with 100 μg of pepsin-digested CII emulsified 1:1 in IFA. After 35 days, mice received a second injection with 50 μg of pepsin-digested CII in IFA.

Mice were then scored at least 3 times a week for development of chronic arthritis. Many, but not all of the mice developed a chronic relapsing disease course characterized by periods of recurrence of active arthritis. These relapses appeared without prediction, lasted for a few weeks at a time, and seemed to occur on a life-long basis. The variability of the arthritis effect in the cohort was mainly due to genetic heterogeneity (the mice were N2 animals, due to an experimental design aimed at mimicking the genetic situation in humans).

To coordinate the recurrence of relapses, mice were reimmunized with CII during the chronic relapsing phase. When the mice were 12-14 months old, animals that had chronic relapsing disease but that presently had no active disease relapse were randomly mixed and sorted into four equal-sized groups. To induce a controlled arthritis relapse, the mice were subcutaneously injected between the scapulae on day-21 (day 259 after the first CII immunization) with either 100 μg of MBP-C5a in PBS (n=24) or with PBS only, each emulsified 1:1 in CFA (n=12). Animals received a booster injection of either 50 μg of MBP-C5a in PBS or PBS alone (each in CFA) on day-3. On day 0 (day 280 after the first CII immunization), animals in both groups were intradermally injected at the root of the tail with 50 μg of pepsin-digested CII emulsified 1:1 in IFA. A second booster injection of 50 μg MBP-C5a in PBS, or PBS only, was administered on day 21 (day 301 after the first CII immunization). In addition, blood samples were obtained by reorbital puncture on day-21 and day 0.

Figure 10:
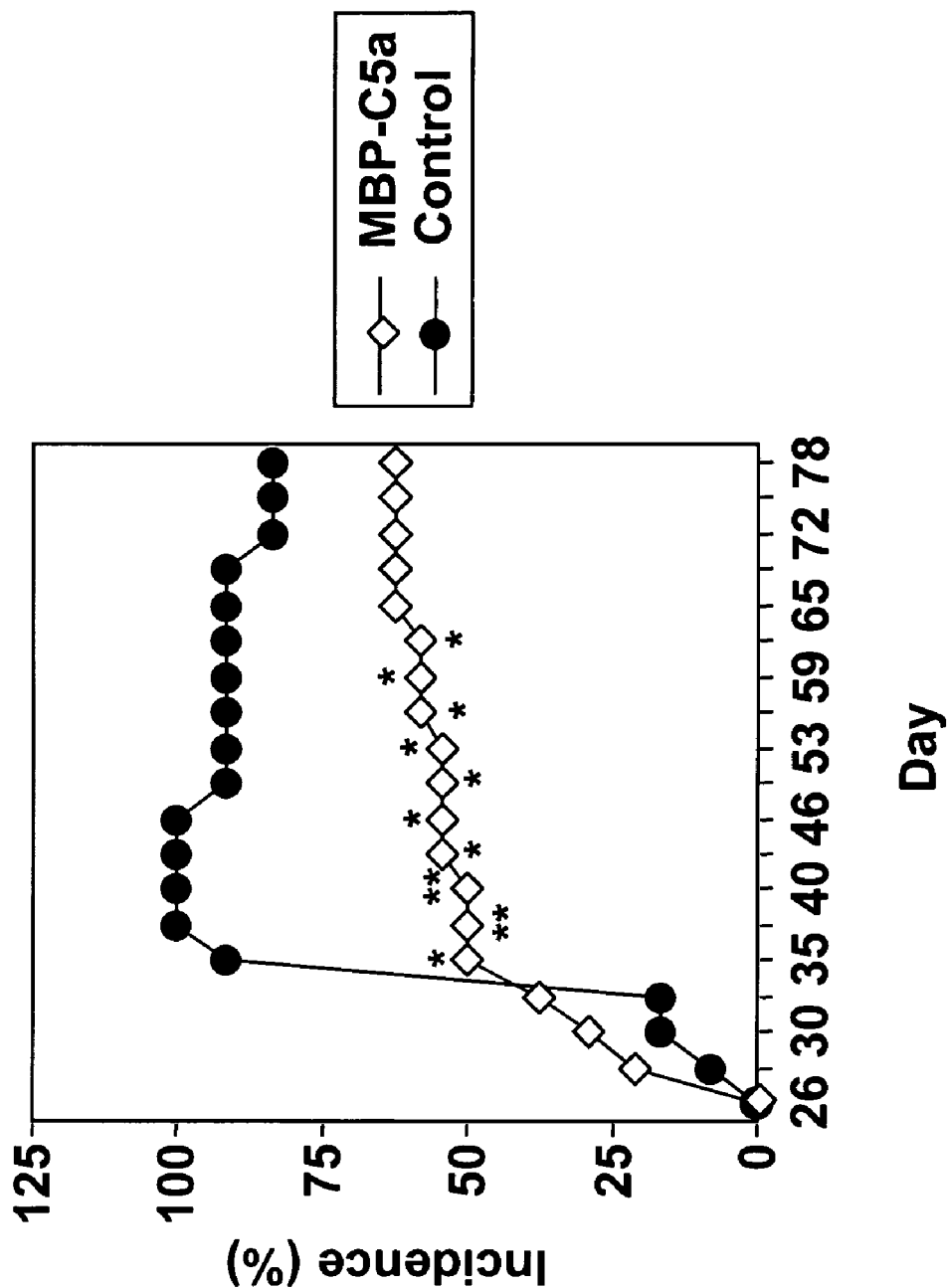
FIG. 10 is a graph plotting the percent incidence of chronic collagen-induced arthritis in control mice (filled circles) and in mice vaccinated with a MBP-C5a fusion polypeptide (open diamonds). *, $p<0.05$; **, $p<0.01$.
Figure 11:
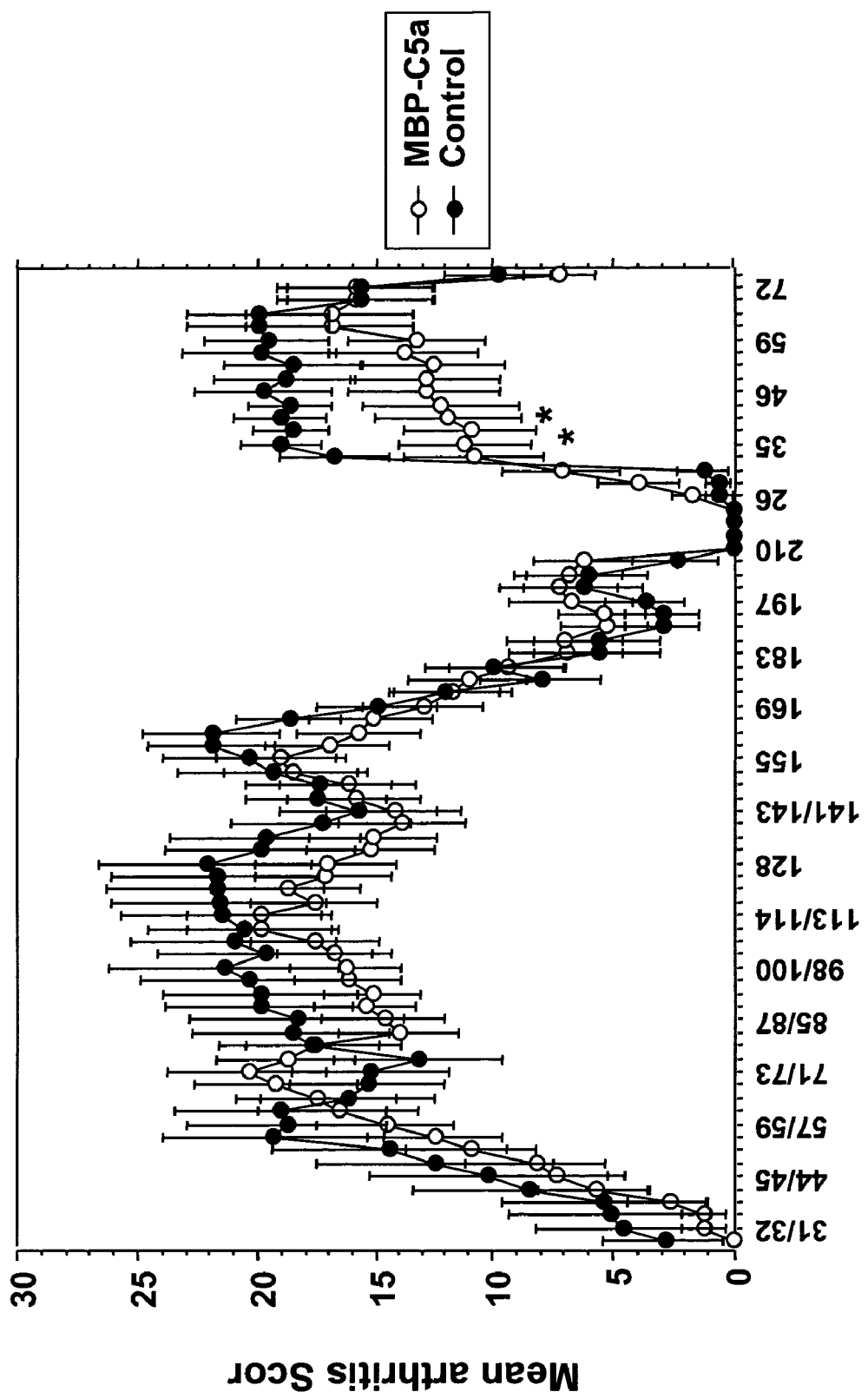
FIG. 11 is a graph plotting the mean score for chronic collagen-induced arthritis in control mice (filled circles) and in mice vaccinated with a MBP-C5a fusion polypeptide (open circles). *, $p<0.05$.

Animals were scored blindly using the scoring system described above, resulting in an arthritis score of 0-60 for each mouse. The experiment was terminated at day 358 after the first CII immunization. These studies revealed that while all of the control mice exhibited arthritis symptoms, especially around day 40, only 50% of the mice immunized with MBP-C5a exhibited chronic arthritis (p<0.05; FIG. 10). In addition, the mean arthritis score was determined for the two groups from the beginning of the study (i.e., from the first injection of CII) through the end of the study more then 358 days later and day 78 after reinduction or relapse (FIG. 11). The mean arthritis score was not significantly different between the two groups until immunization with MBP-C5a, after which the mean arthritis score for the treated group was significantly lower than for the control group (P<0.05; FIG. 11). These results demonstrate that the MBP-C5a fusion polypeptide was able to reduce the incidence of chronic relapsing arthritis in the treated animals.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising an adjuvant and a polypeptide, wherein said polypeptide comprises a self C5 amino acid segment and a non-self amino acid segment, wherein said non-self amino acid segment comprises a maltose binding protein amino acid segment.

2. The composition of claim 1, wherein the length of said non-self amino acid segment is less than 300 amino acids.

3. The composition of claim 1, wherein the length of said non-self amino acid segment is less than 250 amino acids.

4. The composition of claim 1, wherein the length of said non-self amino acid segment is less than 200 amino acids.

5. The composition of claim 1, wherein said self C5 amino acid segment comprises a self C5a amino acid segment.

* * * * *

SEQUENCE LISTING

```
<160> NUMBER OF SEQ ID NOS: 4

<210> SEQ ID NO 1
<211> LENGTH: 5403
<212> TYPE: DNA
<213> ORGANISM: Mus musculus

<400> SEQUENCE: 1
gccgctacca gccatgggtc tttggggaat actttgtctt ttaattttcc tggacaaaac      60
ttggggacag gaacaaacct acgtcatttc agcacccaaa atcctccggg tcggctcgtc     120
tgaaaatgtg gtaattcaag tccatggcta cactgaagca tttgatgcaa ctctttctct     180
aaaaagctat cctgacaaaa aagtcacctt ctcttcaggc tatgttaatt tgtccccgga     240
aaacaaattc caaaacgcgg cactgttgac actacagccc aatcaagttc ctagagaaga     300
```

-continued

```
aagcccagtc tctcacgtgt atctggaagt tgtgtcaaaa cacttttcaa aatcaaagaa    360
aataccaatt acctataaca atggaattct cttcatccat acagacaaac ctgtttacac    420
gccggaccag tcagtaaaga tcagagtcta ttctctgggt gacgacttga agccagccaa    480
acgggagact gtcttaactt tcatagaccc cgaaggatca gaagttgaca ttgtagaaga    540
aaatgattac accggaatta tctctttttcc tgacttcaag attccatcta atcccaagta    600
tggtgtttgg acaattaaag ctaactataa gaaggatttt acaacaactg gaactgcata    660
ctttgaaatt aaagaatatg tcttgccacg attctctgtt tcaatagaac tagaaagaac    720
cttcattggc tataaaaact ttaagaactt tgaaatcact gtgaaagcaa gatattttta    780
taataaagtg gtacctgatg ctgaagtgta tgccttttt ggattgagag aggacataaa     840
agatgaggag aagcagatga tgcacaaagc cacacaagcc gcaaagttgg ttgacggagt    900
tgctcagatc tcttttgatt ctgaaacagc agttaaagag ctgtcctaca acagtctaga    960
agacttaaac aacaagtacc tttatattgc agtaacagtc acagaatctt caggtggatt   1020
ttcagaagag gcagaaatcc ctggagtcaa atatgtcctc tctccctaca cactgaattt   1080
ggtcgctact cctctttttcg tgaagcccgg gattccattt tccatcaagg cacaggttaa   1140
agattcactc gagcaggcgg taggaggggt cccagtaact ctgatggcac aaacagtcga   1200
tgtgaatcaa gagacatctg acttggaaac aaagaggagc atcactcatg acactgatgg   1260
agtagctgtg tttgtgctga acctcccatc aaatgtgacg gtgctaaagt ttgagatcag   1320
aactgatgac ccagaacttc ccgaagaaaa tcaagccagc aaagagtacg aagcagttgc   1380
gtactcgtct ctcagccaaa gttacattta catcgcttgg actgaaaact acaagcccat   1440
gcttgtggga aatacctga atattatggt tacccccaag agcccatata tcgacaaaat    1500
aactcactat aattacttga tttatccaa aggcaaaatt gtacagtacg gcacaagaga    1560
gaaacttttc tcctcaactt atcaaaatat aaatattcca gtgacacaga acatggttcc   1620
ttcagcacga ctcctggtct attacatagt cacaggggag caaacagcag aattagtggc   1680
tgacgcagtc tggataaaata ttgaggagaa gtgtggcaac cagctccagg tccatctgtc   1740
tccagatgaa tatgtgtatt ctccaggcca aactgtgtcc cttgacatgg tgactgaagc   1800
agactcatgg gtagcactat cagcagtgga cagagctgtg tataaagtcc agggaaacgc   1860
caaaagggcc atgcaaagag tctttcaagc tttggatgaa aagagtgacc tgggctgtgg   1920
ggcaggtggt ggccatgaca atgcagatgt attccatcta gctgggctca ccttcctcac   1980
caacgcaaac gcagatgact cccattatcg tgatgactct tgtaaagaaa ttctcaggtc   2040 aaaagagaaac ctgcatctcc taaggcagaa aatagaagaa caagctgcta agtacaaaca   2100
tagtgtgcca aagaaatgct gctatgacgg agcccgagtg aacttctacg aaacctgtga   2160
ggagcgagtg gccgggtta ccataggccc tctctgcatc agggccttca acgagtgctg    2220
tactattgcg aacaagatcc gaaaagaaag ccccataaa cctgtccaac tgggaaggat    2280
ccacattaag accctgttac cagtgatgaa ggcagatatc cgaagctact ttccagagag   2340
ctggctatgg gaaattcatc gcgttcccaa aagaaaacag ctgcaggtca cgctgcctga   2400
ctcactaacg acttgggaaa ttcaaggcat tggcatttca gacaatggta tatgtgttgc   2460
tgatacactc aaggcaaagg tgttcaaaga agtcttcctg gagatgaaca taccatattc   2520
tgttgtgcga ggagaacaga tccaattgaa aggaactgtt tacaactata tgacctcagg   2580
gacaaagttc tgtgttaaaa tgtctgctgt ggaggggatc tgcacttcag gaagctcagc   2640
```

```
tgctagcctt cacacctcca ggccctccag atgtgtgttc cagaggatag agggctcgtc    2700
cagtcacttg gtgaccttca ccctgcttcc tctggaaatt ggccttcact ccataaactt    2760
ctcactagag acctcatttg ggaaagacat cttagtaaag acattacggg tagtgccaga    2820
aggagtcaag agggaaagct atgccggcgt gattctggac cctaagggaa ttcgtggtat    2880
tgttaacaga cgaaaggaat tcccatacag gatcccatta gatttggtcc ccaagaccaa    2940
agttgaaagg attttgagtg tcaaaggact gcttgtaggg gagttcttgt ccacggttct    3000
gagtaaggaa ggcatcaaca tcctaaccca cctccccaag ggcagtgcag aggcagagct    3060
catgagcata gctccggtgt tctatgtttt ccactacctg gaagcaggaa accattggaa    3120
tattttctat cctgatacac tgagtaaaag acagagcctg gagaaaaaaa taaaacaagg    3180
ggtggtgagc gtcatgtcct acagaaacgc tgactattcc tacagcatgt ggaagggggc    3240
gagcgctagt acctggctga cagcttttgc tctgagagtg cttggacagg tggccaagta    3300
tgtaaaacag gatgaaaact caatttgtaa ctctttgcta tggctggttg agaagtgtca    3360
gctggaaaac ggctctttca aggaaaattc ccaatatcta ccaataaaat tacagggtac    3420
tttgcctgct gaagcccaag agaaaacttt gtatcttaca gccttttctg tgattggaat    3480
tagaaaggca gttgacatat gccccaccat gaaaatccac acagcgctag ataaagccga    3540
ctccttcctg cttgaaaaca ccctgccatc caagagcacc ttcacactgg ccattgtagc    3600
ctatgctctt tccctaggag acagaaccca cccgaggttt cgtctaattg tgtcggccct    3660
gaggaaggaa gcttttgtta aaggtgatcc gcccatttac cgttactgga gagataccct    3720
caaacgtcca gacagctctg tgcccagcag cggcacagca ggtatggttg aaaccacagc    3780
ctatgctttg ctcgccagcc tgaaactgaa ggatatgaat tacgccaacc ccatcatcaa    3840
gtggctatct gaagagcaga ggtatggagg cggcttttat tccacccagg atacgattaa    3900
tgccatcgag ggcctgacag aatattcact cctgttaaaa caaattcatt tggatatgga    3960
catcaatgtc gcctacaaac acgaaggtga cttccacaag tataaggtga cagagaagca    4020
tttcctgggg aggccagtgg aggtatctct caatgatgac cttgttgtca gcacaggcta    4080
cagcagtggc ttggccacag tatatgtaaa aactgtggtt cacaaaatta gtgtctctga    4140
ggaattttgc agcttttact tgaaaattga tacccaagat attgaagcat ccagccactt    4200
caggctcagt gactctggat tcaagcgcat aatagcatgt gccagctaca gcccagcaa    4260 ggaggagtca acatccgggt cctcccatgc agtaatggat atatcactgc cgactggaat    4320
cggagcaaac gaggaagatt tacgggctct tgtggaagga gtggatcaac tactaactga    4380
ttaccagatc aaagatggcc atgtcattct gcaactgaat tcgatcccct ccagagattt    4440
cctctgtgtc cggttccgga tatttgaact tttccaagtt gggtttctga atcctgctac    4500
cttcacggtg tacgagtatc acagaccaga taagcagtgc accatgattt atagcatttc    4560
tgacaccagg cttcagaaag tctgtgaagg agcagcttgc acatgtgtgg aagctgactg    4620
tgcgcaactg caggcagaag tagacctagc catctctgca gactccagaa aagagaaagc    4680
ctgtaaacca gagactgcat atgcttataa agtcaggatc acatcagcca ctgaagaaaa    4740 tgttttttgtc aagtacactg cgactcttct ggtcacttac aaaacagggg aagctgctga    4800
tgagaattcg gaggtcacct tcattaaaaa gatgagctgt accaatgcca acctggtgaa    4860
agggaagcag tatttaatca tgggcaaaga ggttctgcag atcaaacaca atttcagttt    4920
caagtatata taccctctag attcctccac ctggattgaa tattggccca cagacacaac    4980
gtgtccatcc tgtcaagcat ttgtagagaa tttgaataac tttgctgaag acctcttttt    5040
```

```
aaacagctgt gaatgaaaag ttctgctgca cgaagattcc tcctgcggcg gggggattgc   5100
tcctcctctg gcttggaaac ctagcctaga atcagataca ctttctttag agtaaagcac   5160
aagctgatga gttacgactt tgtgaaatgg atagccttga ggggaggcga aaacaggtcc   5220
cccaaggcta tcagatgtca gtgccaatag actgaaacaa gtctgtaaag ttagcagtca   5280
ggggtgttgg ttggggccgg aagaagagac ccactgaaac tgtagcccct tatcaaaaca   5340
tatccttgct tgaaagaaaa ataccaagga cagaaaatgc cataaaatct tgactttgca   5400
ctc                                                                 5403

<210> SEQ ID NO 2
<211> LENGTH: 1680
<212> TYPE: PRT
<213> ORGANISM: Mus musculus

<400> SEQUENCE: 2
```

Met Gly Leu Trp Gly Ile Leu Cys Leu Leu Ile Phe Leu Asp Lys Thr
 1               5                  10                  15

Trp Gly Gln Glu Gln Thr Tyr Val Ile Ser Ala Pro Lys Ile Leu Arg
            20                  25                  30

Val Gly Ser Ser Glu Asn Val Val Ile Gln Val His Gly Tyr Thr Glu
        35                  40                  45

Ala Phe Asp Ala Thr Leu Ser Leu Lys Ser Tyr Pro Asp Lys Lys Val
    50                  55                  60

Thr Phe Ser Ser Gly Tyr Val Asn Leu Ser Pro Glu Asn Lys Phe Gln
65                  70                  75                  80

Asn Ala Ala Leu Leu Thr Leu Gln Pro Asn Gln Val Pro Arg Glu Glu
                85                  90                  95

Ser Pro Val Ser His Val Tyr Leu Glu Val Val Ser Lys His Phe Ser
            100                 105                 110

Lys Ser Lys Lys Ile Pro Ile Thr Tyr Asn Asn Gly Ile Leu Phe Ile
        115                 120                 125

His Thr Asp Lys Pro Val Tyr Thr Pro Asp Gln Ser Val Lys Ile Arg
    130                 135                 140

Val Tyr Ser Leu Gly Asp Asp Leu Lys Pro Ala Lys Arg Glu Thr Val
145                 150                 155                 160

Leu Thr Phe Ile Asp Pro Glu Gly Ser Glu Val Asp Ile Val Glu Glu
                165                 170                 175

Asn Asp Tyr Thr Gly Ile Ile Ser Phe Pro Asp Phe Lys Ile Pro Ser
            180                 185                 190

Asn Pro Lys Tyr Gly Val Trp Thr Ile Lys Ala Asn Tyr Lys Lys Asp
        195                 200                 205

Phe Thr Thr Thr Gly Thr Ala Tyr Phe Glu Ile Lys Glu Tyr Val Leu
    210                 215                 220

Pro Arg Phe Ser Val Ser Ile Glu Leu Glu Arg Thr Phe Ile Gly Tyr
225                 230                 235                 240

Lys Asn Phe Lys Asn Phe Glu Ile Thr Val Lys Ala Arg Tyr Phe Tyr
                245                 250                 255

Asn Lys Val Val Pro Asp Ala Glu Val Tyr Ala Phe Gly Leu Arg
            260                 265                 270

Glu Asp Ile Lys Asp Glu Gly Lys Gln Met Met His Lys Ala Thr Gln
        275                 280                 285

Ala Ala Lys Leu Val Asp Gly Val Ala Gln Ile Ser Phe Asp Ser Glu
    290                 295                 300

-continued

```
Thr Ala Val Lys Glu Leu Ser Tyr Asn Ser Leu Glu Asp Leu Asn Asn
305                 310                 315                 320

Lys Tyr Leu Tyr Ile Ala Val Thr Val Thr Glu Ser Ser Gly Gly Phe
                325                 330                 335

Ser Glu Glu Ala Glu Ile Pro Gly Val Lys Tyr Val Leu Ser Pro Tyr
            340                 345                 350

Thr Leu Asn Leu Val Ala Thr Pro Leu Phe Val Lys Pro Gly Ile Pro
        355                 360                 365

Phe Ser Ile Lys Ala Gln Val Lys Asp Ser Leu Glu Gln Ala Val Gly
    370                 375                 380

Gly Val Pro Val Thr Leu Met Ala Gln Thr Val Asp Val Asn Gln Glu
385                 390                 395                 400

Thr Ser Asp Leu Glu Thr Lys Arg Ser Ile Thr His Asp Thr Asp Gly
                405                 410                 415

Val Ala Val Phe Val Leu Asn Leu Pro Ser Asn Val Thr Val Leu Lys
            420                 425                 430

Phe Glu Ile Arg Thr Asp Asp Pro Glu Leu Pro Glu Glu Asn Gln Ala
        435                 440                 445

Ser Lys Glu Tyr Glu Ala Val Ala Tyr Ser Ser Leu Ser Gln Ser Tyr
    450                 455                 460

Ile Tyr Ile Ala Trp Thr Glu Asn Tyr Lys Pro Met Leu Val Gly Glu
465                 470                 475                 480

Tyr Leu Asn Ile Met Val Thr Pro Lys Ser Pro Tyr Ile Asp Lys Ile
                485                 490                 495

Thr His Tyr Asn Tyr Leu Ile Leu Ser Lys Gly Lys Ile Val Gln Tyr
            500                 505                 510

Gly Thr Arg Glu Lys Leu Phe Ser Ser Thr Tyr Gln Asn Ile Asn Ile
        515                 520                 525

Pro Val Thr Gln Asn Met Val Pro Ser Ala Arg Leu Leu Val Tyr Tyr
    530                 535                 540

Ile Val Thr Gly Glu Gln Thr Ala Glu Leu Val Ala Asp Ala Val Trp
545                 550                 555                 560

Ile Asn Ile Glu Glu Lys Cys Gly Asn Gln Leu Gln Val His Leu Ser
                565                 570                 575

Pro Asp Glu Tyr Val Tyr Ser Pro Gly Gln Thr Val Ser Leu Asp Met
            580                 585                 590

Val Thr Glu Ala Asp Ser Trp Val Ala Leu Ser Ala Val Asp Arg Ala
        595                 600                 605

Val Tyr Lys Val Gln Gly Asn Ala Lys Arg Ala Met Gln Arg Val Phe
    610                 615                 620

Gln Ala Leu Asp Glu Lys Ser Asp Leu Gly Cys Gly Ala Gly Gly Gly
625                 630                 635                 640

His Asp Asn Ala Asp Val Phe His Leu Ala Gly Leu Thr Phe Leu Thr
                645                 650                 655

Asn Ala Asn Ala Asp Asp Ser His Tyr Arg Asp Asp Ser Cys Lys Glu
            660                 665                 670

Ile Leu Arg Ser Lys Arg Asn Leu His Leu Leu Arg Gln Lys Ile Glu
        675                 680                 685

Glu Gln Ala Ala Lys Tyr Lys His Ser Val Pro Lys Lys Cys Cys Tyr
    690                 695                 700

Asp Gly Ala Arg Val Asn Phe Tyr Glu Thr Cys Glu Glu Arg Val Ala
705                 710                 715                 720
```

```
Arg Val Thr Ile Gly Pro Leu Cys Ile Arg Ala Phe Asn Glu Cys Cys
                725                 730                 735

Thr Ile Ala Asn Lys Ile Arg Lys Glu Ser Pro His Lys Pro Val Gln
            740                 745                 750

Leu Gly Arg Ile His Ile Lys Thr Leu Pro Val Met Lys Ala Asp
            755                 760                 765

Ile Arg Ser Tyr Phe Pro Glu Ser Trp Leu Trp Glu Ile His Arg Val
            770                 775                 780

Pro Lys Arg Lys Gln Leu Gln Val Thr Leu Pro Asp Ser Leu Thr Thr
785                 790                 795                 800

Trp Glu Ile Gln Gly Ile Gly Ile Ser Asp Asn Gly Ile Cys Val Ala
                805                 810                 815

Asp Thr Leu Lys Ala Lys Val Phe Lys Glu Val Phe Leu Glu Met Asn
            820                 825                 830

Ile Pro Tyr Ser Val Val Arg Gly Glu Gln Ile Gln Leu Lys Gly Thr
            835                 840                 845

Val Tyr Asn Tyr Met Thr Ser Gly Thr Lys Phe Cys Val Lys Met Ser
850                 855                 860

Ala Val Glu Gly Ile Cys Thr Ser Gly Ser Ala Ala Ser Leu His
865                 870                 875                 880

Thr Ser Arg Pro Ser Arg Cys Val Phe Gln Arg Ile Glu Gly Ser Ser
            885                 890                 895

Ser His Leu Val Thr Phe Thr Leu Leu Pro Leu Glu Ile Gly Leu His
            900                 905                 910

Ser Ile Asn Phe Ser Leu Glu Thr Ser Phe Gly Lys Asp Ile Leu Val
            915                 920                 925

Lys Thr Leu Arg Val Val Pro Glu Gly Val Lys Arg Glu Ser Tyr Ala
            930                 935                 940

Gly Val Ile Leu Asp Pro Lys Gly Ile Arg Gly Ile Val Asn Arg Arg
945                 950                 955                 960

Lys Glu Phe Pro Tyr Arg Ile Pro Leu Asp Leu Val Pro Lys Thr Lys
                965                 970                 975

Val Glu Arg Ile Leu Ser Val Lys Gly Leu Leu Val Gly Glu Phe Leu
            980                 985                 990

Ser Thr Val Leu Ser Lys Glu Gly Ile Asn Ile Leu Thr His Leu Pro
            995                 1000                1005

Lys Gly Ser Ala Glu Ala Glu Leu Met Ser Ile Ala Pro Val Phe Tyr
    1010                1015                1020

Val Phe His Tyr Leu Glu Ala Gly Asn His Trp Asn Ile Phe Tyr Pro
1025                1030                1035                1040

Asp Thr Leu Ser Lys Arg Gln Ser Leu Glu Lys Lys Ile Lys Gln Gly
                1045                1050                1055

Val Val Ser Val Met Ser Tyr Arg Asn Ala Asp Tyr Ser Tyr Ser Met
            1060                1065                1070

Trp Lys Gly Ala Ser Ala Ser Thr Trp Leu Thr Ala Phe Ala Leu Arg
        1075                1080                1085

Val Leu Gly Gln Val Ala Lys Tyr Val Lys Gln Asp Glu Asn Ser Ile
            1090                1095                1100

Cys Asn Ser Leu Leu Trp Leu Val Glu Lys Cys Gln Leu Glu Asn Gly
1105                1110                1115                1120

Ser Phe Lys Glu Asn Ser Gln Tyr Leu Pro Ile Lys Leu Gln Gly Thr
        1125                1130                1135

Leu Pro Ala Glu Ala Gln Glu Lys Thr Leu Tyr Leu Thr Ala Phe Ser
```

-continued

```
            1140                1145                1150
Val Ile Gly Ile Arg Lys Ala Val Asp Ile Cys Pro Thr Met Lys Ile
        1155                1160                1165
His Thr Ala Leu Asp Lys Ala Asp Ser Phe Leu Leu Glu Asn Thr Leu
        1170                1175                1180
Pro Ser Lys Ser Thr Phe Thr Leu Ala Ile Val Ala Tyr Ala Leu Ser
1185                1190                1195                1200
Leu Gly Asp Arg Thr His Pro Arg Phe Arg Leu Ile Val Ser Ala Leu
                1205                1210                1215
Arg Lys Glu Ala Phe Val Lys Gly Asp Pro Ile Tyr Arg Tyr Trp
        1220                1225                1230
Arg Asp Thr Leu Lys Arg Pro Asp Ser Ser Val Pro Ser Ser Gly Thr
        1235                1240                1245
Ala Gly Met Val Glu Thr Thr Ala Tyr Ala Leu Leu Ala Ser Leu Lys
        1250                1255                1260
Leu Lys Asp Met Asn Tyr Ala Asn Pro Ile Ile Lys Trp Leu Ser Glu
1265                1270                1275                1280
Glu Gln Arg Tyr Gly Gly Gly Phe Tyr Ser Thr Gln Asp Thr Ile Asn
        1285                1290                1295
Ala Ile Glu Gly Leu Thr Glu Tyr Ser Leu Leu Lys Gln Ile His
        1300                1305                1310
Leu Asp Met Asp Ile Asn Val Ala Tyr Lys His Glu Gly Asp Phe His
        1315                1320                1325
Lys Tyr Lys Val Thr Glu Lys His Phe Leu Gly Arg Pro Val Glu Val
        1330                1335                1340
Ser Leu Asn Asp Asp Leu Val Val Ser Thr Gly Tyr Ser Ser Gly Leu
1345                1350                1355                1360
Ala Thr Val Tyr Val Lys Thr Val Val His Lys Ile Ser Val Ser Glu
                1365                1370                1375
Glu Phe Cys Ser Phe Tyr Leu Lys Ile Asp Thr Gln Asp Ile Glu Ala
        1380                1385                1390
Ser Ser His Phe Arg Leu Ser Asp Ser Gly Phe Lys Arg Ile Ile Ala
        1395                1400                1405
Cys Ala Ser Tyr Lys Pro Ser Lys Glu Glu Ser Thr Ser Gly Ser Ser
        1410                1415                1420
His Ala Val Met Asp Ile Ser Leu Pro Thr Gly Ile Gly Ala Asn Glu
1425                1430                1435                1440
Glu Asp Leu Arg Ala Leu Val Glu Gly Val Asp Gln Leu Leu Thr Asp
                1445                1450                1455
Tyr Gln Ile Lys Asp Gly His Val Ile Leu Gln Leu Asn Ser Ile Pro
        1460                1465                1470
Ser Arg Asp Phe Leu Cys Val Arg Phe Arg Ile Phe Glu Leu Phe Gln
        1475                1480                1485
Val Gly Phe Leu Asn Pro Ala Thr Phe Thr Val Tyr Glu Tyr His Arg
        1490                1495                1500
Pro Asp Lys Gln Cys Thr Met Ile Tyr Ser Ile Ser Asp Thr Arg Leu
1505                1510                1515                1520
Gln Lys Val Cys Glu Gly Ala Ala Cys Thr Cys Val Glu Ala Asp Cys
                1525                1530                1535
Ala Gln Leu Gln Ala Glu Val Asp Leu Ala Ile Ser Ala Asp Ser Arg
        1540                1545                1550
Lys Glu Lys Ala Cys Lys Pro Glu Thr Ala Tyr Ala Tyr Lys Val Arg
        1555                1560                1565
```

```
Ile Thr Ser Ala Thr Glu Glu Asn Val Phe Val Lys Tyr Thr Ala Thr
    1570                1575                1580

Leu Leu Val Thr Tyr Lys Thr Gly Glu Ala Ala Asp Glu Asn Ser Glu
1585                1590                1595                1600

Val Thr Phe Ile Lys Lys Met Ser Cys Thr Asn Ala Asn Leu Val Lys
                1605                1610                1615

Gly Lys Gln Tyr Leu Ile Met Gly Lys Glu Val Leu Gln Ile Lys His
            1620                1625                1630

Asn Phe Ser Phe Lys Tyr Ile Tyr Pro Leu Asp Ser Ser Thr Trp Ile
        1635                1640                1645

Glu Tyr Trp Pro Thr Asp Thr Thr Cys Pro Ser Cys Gln Ala Phe Val
    1650                1655                1660

Glu Asn Leu Asn Asn Phe Ala Glu Asp Leu Phe Leu Asn Ser Cys Glu
1665                1670                1675                1680

<210> SEQ ID NO 3
<211> LENGTH: 1434
<212> TYPE: DNA
<213> ORGANISM: Artificial Sequence
<220> FEATURE:
<223> OTHER INFORMATION: PCR product encoding fusion protein

<400> SEQUENCE: 3
gaattccacc atcaccatca ccatctcgag ccgcgggccg atatgaaaat cgaagaaggt      60
aaactggtaa tctggattaa cggcgataaa ggctataacg gtctcgctga agtcggtaag     120
aaattcgaga agataccgg aattaaagtc accgttgagc atccggataa actggaagag     180
aaattcccac aggttgcggc aactggcgat ggccctgaca ttatcttctg ggcacacgac     240
cgctttggtg gctacgctca atctggcctg ttggctgaaa tcaccccgga caaagcgttc     300
caggacaagc tgtatccgtt tacctgggat gccgtacgtt acaacggcaa gctgattgct     360
tacccgatcg ctgttgaagc gttatcgctg atttataaca agatctgct gccgaacccg     420
ccaaaaaccct gggaagagat cccggcgctg ataaagaac tgaaagcgaa aggtaagagc     480
gcgctgatgt tcaacctgca gaaccgtac ttcacctggc cgctgattgc tgctgacggg     540
ggttatgcgt tcaagtatga aaacggcaag tacgacatta agacgtggg cgtggataac     600
gctggcgcga agcgggtcct gaccttcctg gttgacctga ttaaaaacaa acacatgaat     660
gcagacaccg attactccat cgcagaagct gcctttaata aaggcgaaac agcgatgacc     720
atcaacggcc cgtgggcatg gtccaacatc gacaccagca agtgaatta tggtgtaacg     780
gtactgccga ccttcaaggg tcaaccatcc aaaccgttcg ttggcgtgct gagcgcaggt     840
attaacgccg ccagtccgaa caaagagctg gcaaagagt tcctcgaaaa ctatctgctg     900
actgatgaag tctggaagc ggttaataaa gacaaaccgc tgggtgccgt agcgctgaag     960
tcttacgagg aagagttggc gaaagatcca cgtattgccg ccactatgga aaacgcccag    1020
aaaggtgaaa tcatgccgaa catcccgcag atgtccgctt ctggtatgc cgtgcgtact    1080
gcggtgatca acgccgccag cggtcgtcag actgtcgatg aagccctgaa agacgcgcag    1140
actaattcga gctcgaacaa caacaacaat aacaataaca caacctcgg gatcgaggga    1200
aggctgctaa gcagaaaat agaagaacaa gctgctaagt acaaacatag tgtgccaaag    1260
aaatgctgct atgacggagc ccgagtgaac ttctacgaaa cctgtgagga gcgagtggcc    1320
cgggttacca taggccctct ctgcatcagg gccttcaacg agtgctgtac tattgcgaac    1380
aagatccgaa agaaagccc catagaacct gtccaactgg aaggtaagt cgag            1434
```

<210> SEQ ID NO 4
<211> LENGTH: 475
<212> TYPE: PRT
<213> ORGANISM: Artificial Sequence
<220> FEATURE:
<223> OTHER INFORMATION: fusion protein

<400> SEQUENCE: 4

```
Glu Phe His His His His His His Leu Glu Pro Arg Ala Asp Met Lys
1               5                   10                  15

Ile Glu Glu Gly Lys Leu Val Ile Trp Ile Asn Gly Asp Lys Gly Tyr
            20                  25                  30

Asn Gly Leu Ala Glu Val Gly Lys Lys Phe Glu Lys Asp Thr Gly Ile
        35                  40                  45

Lys Val Thr Val Glu His Pro Asp Lys Leu Glu Glu Lys Phe Pro Gln
    50                  55                  60

Val Ala Ala Thr Gly Asp Gly Pro Asp Ile Ile Phe Trp Ala His Asp
65                  70                  75                  80

Arg Phe Gly Gly Tyr Ala Gln Ser Gly Leu Leu Ala Glu Ile Thr Pro
                85                  90                  95

Asp Lys Ala Phe Gln Asp Lys Leu Tyr Pro Phe Thr Trp Asp Ala Val
            100                 105                 110

Arg Tyr Asn Gly Lys Leu Ile Ala Tyr Pro Ile Ala Val Glu Ala Leu
        115                 120                 125

Ser Leu Ile Tyr Asn Lys Asp Leu Leu Pro Asn Pro Pro Lys Thr Trp
    130                 135                 140

Glu Glu Ile Pro Ala Leu Asp Lys Glu Leu Lys Ala Lys Gly Lys Ser
145                 150                 155                 160

Ala Leu Met Phe Asn Leu Gln Glu Pro Tyr Phe Thr Trp Pro Leu Ile
                165                 170                 175

Ala Ala Asp Gly Gly Tyr Ala Phe Lys Tyr Glu Asn Gly Lys Tyr Asp
            180                 185                 190

Ile Lys Asp Val Gly Val Asp Asn Ala Gly Ala Lys Ala Gly Leu Thr
        195                 200                 205

Phe Leu Val Asp Leu Ile Lys Asn Lys His Met Asn Ala Asp Thr Asp
    210                 215                 220

Tyr Ser Ile Ala Glu Ala Ala Phe Asn Lys Gly Glu Thr Ala Met Thr
225                 230                 235                 240

Ile Asn Gly Pro Trp Ala Trp Ser Asn Ile Asp Thr Ser Lys Val Asn
                245                 250                 255

Tyr Gly Val Thr Val Leu Pro Thr Phe Lys Gly Gln Pro Ser Lys Pro
            260                 265                 270

Phe Val Gly Val Leu Ser Ala Gly Ile Asn Ala Ala Ser Pro Asn Lys
        275                 280                 285

Glu Leu Ala Lys Glu Phe Leu Glu Asn Tyr Leu Leu Thr Asp Glu Gly
    290                 295                 300

Leu Glu Ala Val Asn Lys Asp Lys Pro Leu Gly Ala Val Ala Leu Lys
305                 310                 315                 320

Ser Tyr Glu Glu Glu Leu Ala Lys Asp Pro Arg Ile Ala Ala Thr Met
                325                 330                 335

Glu Asn Ala Gln Lys Gly Glu Ile Met Pro Asn Ile Pro Gln Met Ser
            340                 345                 350

Ala Phe Trp Tyr Ala Val Arg Thr Ala Val Ile Asn Ala Ala Ser Gly
        355                 360                 365
```

-continued

```
Arg Gln Thr Val Asp Glu Ala Leu Lys Asp Ala Gln Thr Asn Ser Ser
    370                 375                 380

Ser Asn Asn Asn Asn Asn Asn Asn Asn Asn Asn Leu Gly Ile Glu Gly
385                 390                 395                 400

Arg Leu Leu Arg Gln Lys Ile Glu Glu Gln Ala Ala Lys Tyr Lys His
                405                 410                 415

Ser Val Pro Lys Lys Cys Cys Tyr Asp Gly Ala Arg Val Asn Phe Tyr
            420                 425                 430

Glu Thr Cys Glu Glu Arg Val Ala Arg Val Thr Ile Gly Pro Leu Cys
        435                 440                 445

Ile Arg Ala Phe Asn Glu Cys Cys Thr Ile Ala Asn Lys Ile Arg Lys
    450                 455                 460

Glu Ser Pro His Lys Pro Val Gln Leu Gly Arg
465                 470                 475
```